United States Patent

Howard et al.

[11] Patent Number: 5,854,262
[45] Date of Patent: *Dec. 29, 1998

[54] AMINOMETHYLENE SUBSTITUTED NON-AROMATIC HETEROCYCLES AND USE AS SUBSTANCE P ANTAGONISTS

[75] Inventors: Harry R. Howard, Bristol; Brian T. O'Neill, Westbrook, both of Conn.

[73] Assignee: Pfizer Inc., New York, N.Y.

[ * ] Notice: The terminal 9 months of this patent has been disclaimed.

[21] Appl. No.: 522,230

[22] PCT Filed: Oct. 7, 1993

[86] PCT No.: PCT/US93/09407

§ 371 Date: May 25, 1995

§ 102(e) Date: May 25, 1995

[87] PCT Pub. No.: WO94/13663

PCT Pub. Date: Jun. 23, 1994

[51] Int. Cl.[6] ............... A61K 31/445; C07D 211/36; C07D 211/56
[52] U.S. Cl. ............ 514/329; 514/326; 514/327; 546/194; 546/209; 546/210
[58] Field of Search .................... 514/256, 293, 514/305, 314, 318, 326, 327, 329; 544/331, 335; 546/133, 134, 135, 194, 209, 210

[56] References Cited

U.S. PATENT DOCUMENTS 5,162,339  11/1992  Lowe et al. .............. 514/305
5,232,929  8/1993  Desai et al. .............. 514/314

FOREIGN PATENT DOCUMENTS 9206079  4/1992  WIPO.

*Primary Examiner*—Yogendra N. Gupta
*Attorney, Agent, or Firm*—Peter C. Richardson; Paul H. Ginsburg; Bryan C. Zielinski

[57] ABSTRACT

A compound of the formula

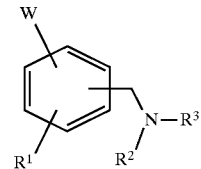

or a pharmaceutically acceptable salt thereof;

W is hydrogen, $(C_1-C_6)$alkyl optionally substituted with from one to three fluorine atoms, $-S(O)_v-(C_1-C_6)$alkyl wherein v is zero, one or two, halo, benzyloxy or $(C_1-C_6)$alkoxy optionally substituted with from one to three fluorine atoms;

$R^1$ is a 4, 5 or 6 membered heterocyclic ring containing from one to three heteroatoms selected from oxygen, nitrogen and sulfur, wherein said heterocyclic ring contains from zero to three double bonds and is optionally substituted with one or two substituents independently selected from $(C_1-C_6)$ alkyl optionally substituted with from one to three fluorine atoms and $(C_1-C_6)$ alkoxy optionally substituted with from one to three fluorine atoms;

$R^2$ is hydrogen or $-CO_2(C_1-C_{10})$alkyl;

$R^3$ is

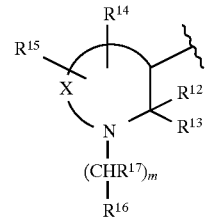

14 Claims, No Drawings

AMINOMETHYLENE SUBSTITUTED NON-AROMATIC HETEROCYCLES AND USE AS SUBSTANCE P ANTAGONISTS

BACKGROUND OF THE INVENTION

The present invention relates to novel aminomethylene substituted non-aromatic heterocycles, pharmaceutical compositions comprising such compounds and the use of such compounds in the treatment and prevention of inflammatory and central nervous system disorders, as well as several other disorders. The pharmaceutically active compounds of this invention are substance P receptor antagonists. This invention also relates to novel intermediates used in the synthesis of such substance P receptor antagonists.

Substance P is a naturally occurring undecapeptide belonging to the tachykinin family of peptides, the latter being named because of their prompt stimulatory action on smooth muscle tissue. More specifically, substance P is a pharmacologically active neuropeptide that is produced in mammals and possesses a characteristic amino acid sequence that is illustrated by D. F. Veber et al. in U.S. Pat. No. 4,680,283.

The following references refer, collectively, to quinuclidine, piperidine, and azanorbornane derivatives and related compounds that exhibit activity as substance P receptor antagonists: U.S. Pat. No. 5,162,339, which issued on Nov. 11, 1992; U.S. patent application Ser. No. 724,268, filed Jul. 1, 1991; PCT Patent Application PCT/US 91/02853, filed Apr. 25, 1991; PCT Patent Application PCT/US 91/03369, filed May 14, 1991; PCT Patent Application PCT/US 91/05776, filed Aug. 20, 1991; PCT Patent Application PCT/US 92/00113, filed Jan. 17, 1992; PCT Patent Application PCT/US 92/03571, filed May 5, 1992; PCT Patent Application PCT/US 92/03317, filed Apr. 28, 1992; PCT Patent Application PCT/US 92/04697, filed Jun. 11, 1992; United States Patent Application 766,488, filed Sep. 26, 1991; U.S. patent application Ser. No. 790,934, filed Nov. 12, 1991; PCT Patent Application PCT/US 92/04002, filed May 19, 1992; Japanese Patent Application 065337/92, filed Mar. 23, 1992; and U.S. patent application Ser. No. 932,392, filed Aug. 19, 1992.

SUMMARY OF THE INVENTION

The present invention relates to compounds of the formula

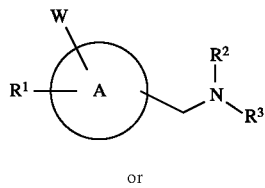

Ia or

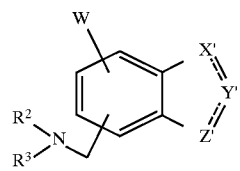

Ib wherein A is a ring system selected from phenyl, naphthyl, thienyl, quinolinyl and indolinyl, and wherein the side chain containing $NR^2R^3$ is attached to a carbon atom of ring system A;

W is hydrogen, $(C_1-C_6)$alkyl optionally substituted with from one to three fluorine atoms, $—S(O)_v—(C_1-C_6)$ alkyl wherein v is zero, one or two, halo, benzyloxy or $(C_1-C_6)$ alkoxy optionally substituted with from one to three fluorine atoms;

$R^1$ is a 4, 5 or 6 membered heterocyclic ring containing from one to three heteroatoms selected from oxygen, nitrogen and sulfur (e.g., thiazolyl, azetidinyl, pyrrolyl, pyrazolyl, 1,2,3-triazolyl, 1,2,4-triazolyl, isothiazolyl, imidazolyl, isoxazolyl, oxazolyl, pyridyl, pyrimidinyl, pyrazolyl or thiophenyl), wherein said heterocyclic ring may contain from zero to three double bonds and may optionally be substituted with one or more substituents, preferably one or two substituents, independently selected from $(C_1-C_6)$ alkyl optionally substituted with from one to three fluorine atoms and $(C_1-C_6)$ alkoxy optionally substituted with from one to three fluorine atoms;

the dotted lines in formula Ib indicate that one of the X'-Y' and Y'-Z' bonds may optionally be a double bond;

X' is selected from =CH—, —CH$_2$—, —O—, —S—, —SO—, —SO$_2$—, —N(R$^4$)—, —NH—, =N—, —CH[(C$_1$-C$_6$)alkyl]—, =C[(C$_1$-C$_6$)alkyl]—, —CH(C$_6$H$_5$)— and =C(C$_6$H$_5$)—;

Y' is selected from C=O, C=NR$^4$, C=S, =CH—, —CH$_2$—, =C[(C$_1$-C$_6$)alkyl]—, —CH[(C$_1$-C$_6$)alkyl]—, =C(C$_6$H$_5$)—, —CH(C$_6$H$_5$)—, =N—, —NH—, —N(R$^4$)—, =C(halo)—, =C(OR$^4$)—, =C(SR$^4$)—, =C(NR$^4$)—, —O—, =C(CF$_3$)—, =C(CH$_2$C$_6$H$_5$)—, —S— and SO$_2$, wherein the phenyl moieties of said =C(C$_6$H$_5$)— and —CH(C$_6$H$_5$)— may optionally be substituted with from one to three substituents independently selected from trifluoromethyl and halo, and wherein the alkyl moieties of said =[(C$_1$-C$_6$)alkyl]— and —CH[C$_1$-C$_6$)alkyl]— may optionally be substituted with from one to three fluorine atoms;

Z' is selected from =CH—, —CH$_2$—, =N—, —NH—, —S—, —N(R$^4$)—, =C(C$_6$H$_5$)—, —CH(C$_6$H$_5$)—, =C[(C$_1$-C$_6$)alkyl]— and —CH[(C$_1$-C$_6$)alkyl]—;

or X', Y' and Z', together with the two carbon atoms shared between the benzo ring and the X'Y'Z' ring, form a fused pyridine or pyrimidine ring;

$R^2$ is hydrogen or $—CO_2(C_1-C_{10})$alkyl;

$R^3$ is selected from

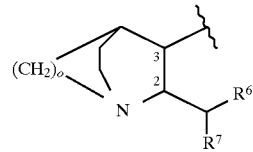

II

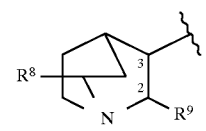

III

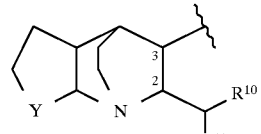

IV

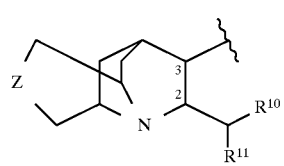

V

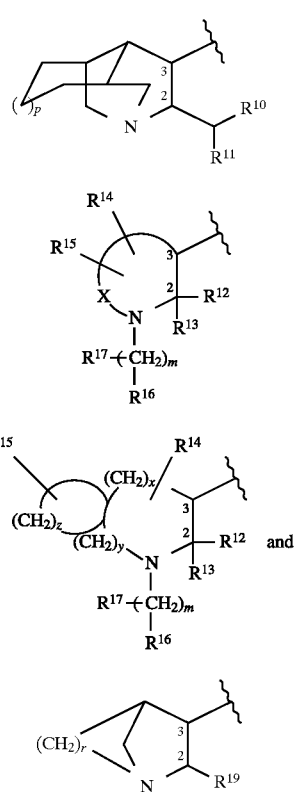

wherein $R^6$ and $R^{10}$ are independently selected from furyl, thienyl, pyridyl, indolyl, biphenyl and phenyl, wherein said phenyl may optionally be substituted with one or two substituents independently selected from halo, $(C_1-C_{10})$ alkyl optionally substituted with from one to three fluorine atoms, $(C_1-C_{10})$ alkoxy optionally substituted with from one to three fluorine atoms, carboxy, benzyloxycarbonyl and $(C_1-C_3)$ alkoxy-carbonyl;

$R^4$ is $(C_1-C_6)$ alkyl or phenyl;

$R^7$ is selected from $(C_3-C_4)$ branched alkyl, $(C_5-C_6)$ branched alkenyl, $(C_5-C_7)$ cycloalkyl, and the radicals named in the definition of $R^6$;

$R^8$ is hydrogen or $(C_1-C_6)$ alkyl;

$R^9$ and $R^{19}$ are independently selected from phenyl, biphenyl, naphthyl, benzhydryl, thienyl and furyl, and $R^9$ and $R^{19}$ may optionally be substituted with from one to three substituents independently selected from halo, $(C_1-C_{10})$ alkyl optionally substituted with from one to three fluorine atoms and $(C_1-C_{10})$ alkoxy optionally substituted with from one to three fluorine atoms;

Y is $(CH_2)_1$ wherein 1 is an integer from one to three, or Y is a group of the formula

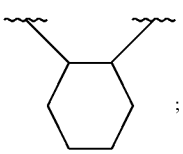 (J)

Z is oxygen, sulfur, amino, $(C_1-C_3)$alkylamino or $(CH_2)_n$ wherein n is zero, one or two;

x is zero, one or two;
y is zero, one or two;
z is three, four or five;
o is two or three;
p is zero or one;
r is one, two or three;

the ring containing $(CH_2)_z$ may contain from zero to three double bonds, and one of the carbon atoms of $(CH_2)_z$ may optionally be replaced by oxygen, sulfur or nitrogen;

$R^{11}$ is thienyl, biphenyl or phenyl optionally substituted with one or two substituents independently selected from halo, $(C_1-C_{10})$ alkyl optionally substituted with from one to three fluorine atoms and $(C_1-C_{10})$ alkoxy optionally substituted with from one to three fluorine atoms;

X is $(CH_2)_q$ wherein q is an integer from 1 to 6, and wherein any one of the carbon—carbon single bonds in said $(CH_2)_q$ may optionally be replaced by a carbon—carbon double bond, and wherein any one of the carbon atoms of said $(CH_2)_q$ may optionally be substituted with $R^{14}$, and wherein any one of the carbon atoms of said $(CH_2)_q$ may optionally be substituted with $R^{15}$;

m is an integer from 0 to 8, and any one of the carbon—carbon single bonds of $(CH_2)_m$, wherein both carbon atoms of such bond are bonded to each other and to another carbon atom of the $(CH_2)_m$ chain, may optionally be replaced by a carbon—carbon double bond or a carbon—carbon triple bond, and any one of the carbon atoms of said $(CH_2)_m$ may optionally be substituted with $R^{17}$;

$R^{12}$ is a radical selected from hydrogen, $(C_1-C_6)$ straight or branched alkyl, $(C_3-C_7)$ cycloalkyl wherein one of the carbon atoms may optionally be replaced by nitrogen, oxygen or sulfur; aryl selected from biphenyl, phenyl, indanyl and naphthyl; heteroaryl selected from thienyl, furyl, pyridyl, thiazolyl, isothiazolyl, oxazolyl, isoxazolyl, triazolyl, tetrazolyl and quinolyl; phenyl-$(C_2-C_6)$ alkyl, benzhydryl and benzyl, wherein the point of attachment on $R^{12}$ is a carbon atom unless $R^{12}$ is hydrogen, and wherein each of said aryl and heteroaryl groups and the phenyl moieties of said benzyl, phenyl-$(C_2-C_6)$ alkyl and benzhydryl may optionally be substituted with one or more substituents independently selected from halo, nitro, $(C_1-C_{10})$ alkyl optionally substituted with from one to three fluorine atoms, $(C_1-C_{10})$ alkoxy optionally substituted with from one to three fluorine atoms, amino, hydroxy-$(C_1-C_6)$alkyl, $(C_1-C_6)$ alkoxy-$(C_1-C_6)$alkyl, $(C_1-C_6)$-alkylamino,

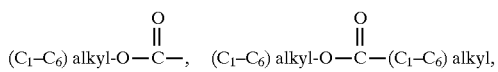

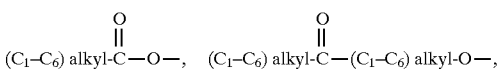

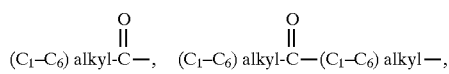

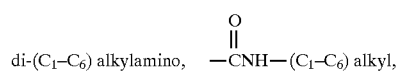

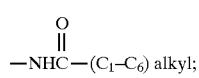

and wherein one of the phenyl moieties of said benzhydryl may optionally be replaced by naphthyl, thienyl, furyl or pyridyl;

$R^{13}$ is hydrogen, phenyl or $(C_1-C_6)$alkyl;

or $R^{12}$ and $R^{13}$, together with the carbon to which they are attached, form a saturated carbocyclic ring having from 3 to 7 carbon atoms wherein one of said carbon atoms that is neither the point of attachment of the spiro ring nor adjacent to such point of attachment may optionally be replaced by oxygen, nitrogen or sulfur;

$R^{14}$ and $R^{15}$ are each independently selected from hydrogen, hydroxy, halo, amino, oxo (=O), cyano, hydroxy-$(C_1-C_6)$alkyl, $(C_1-C_6)$alkoxy-$(C_1-C_6)$alkyl, $(C_1-C_6)$alkylamino,

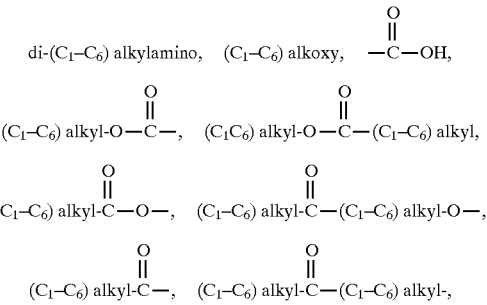

and the radicals set forth in the definition of $R^{12}$;

$R^{16}$ is

$NHCH_2R^{18}$, $SO_2R^{18}$, $CO_2H$ or one of the radicals set forth in any of the definitions of $R^{12}$, $R^{14}$ and $R^{15}$;

$R^{17}$ is oximino (=NOH) or one of the radicals set forth in any of the definitions of $R^{12}$, $R^{14}$ and $R^{15}$; and $R^{18}$ is $(C_1-C_6)$alkyl, hydrogen, phenyl or phenyl $(C_1-C_6)$ alkyl;

with the proviso that (a) when m is 0, one of $R^{16}$ and $R^{17}$ is absent and the other is hydrogen, (b) when $R^3$ is a group of the formula VIII, $R^{14}$ and $R^{15}$ cannot be attached to the same carbon atom, (c) when $R^{14}$ and $R^{15}$ are attached to the same carbon atom, then either each of $R^{14}$ and $R^{15}$ is independently selected from hydrogen, fluoro, $(C_1-C_6)$ alkyl, hydroxy-$(C_1-C_6)$alkyl and $(C_1-C_6)$alkoxy-$(C_1-C_6)$ alkyl, or $R^{14}$ and $R^{15}$, together with the carbon to which they are attached, form a $(C_3-C_6)$ saturated carbocyclic ring that forms a spiro compound with the nitrogen-containing ring to which they are attached; (d) $R^{12}$ and $R^{13}$ can not both be hydrogen, and (e) when $R^{14}$ or $R^{15}$ is attached to a carbon atom of X or $(CH_2)_y$ that is adjacent to the ring nitrogen, then $R^{14}$ or $R^{15}$, respectively, must be a substituent wherein the point of attachment is a carbon atom.

The present invention also relates to the pharmaceutically acceptable acid addition and base salts of compounds of the formulae Ia and Ib (hereinafter referred to, collectively, as compounds of the formula I). The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate) ]salts. The chemical bases which are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium calcium and magnesium, etc.

The fused bicyclic nucleus of compounds of the formula Ib to which W and the $-CH_2NR^2R^3$ sidechain are attached may be, but is not limited to one of the following groups: benzoxazolyl, benzthiazolyl, benzimidazolyl, benzisoxazolyl, benzoisothiazolyl, indazolyl, indolyl, isoquinolinyl, benzofuryl, benzothienyl, oxindolyl, benzoxazolinonyl, benzthiazolinonyl, benzimidazolinonyl, benzimidazoliniminyl, dihydrobenzothienyl-S,S-dioxide, benztriazolyl, benzthiadiazolyl, benzoxadiazolyl, and quinazolinyl.

The term "halo", as used herein, unless otherwise indicated, includes chloro, fluoro, bromo and iodo.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined as above.

The term "tone or more substituents," as used herein, includes from one to the maximum number of substituents possible based on the number of available bonding sites.

Preferred compounds of this invention include those compounds of the formula I wherein the substituents at positions "2" and "3" of the nitrogen containing ring of $R^3$ are in a cis configuration. When $R^3$ is a group of the formula VII or VIII, "a cis configuration", as used herein, means that the non-hydrogen substituent at position "3" is cis to $R^{12}$.

Other preferred compounds of this invention include those compounds of the formula Ia wherein $R^3$ is a group of the formula III, VII or IX; $R^2$ is hydrogen; A is phenyl or indolinyl; W is $(C_1-C_3)$ alkoxy optionally substituted with from one to five fluorine atoms; and $R^1$ is thiazolyl, imidazolyl, thiadiazolyl, pyrrolyl, oxazolyl, pyridyl, pyrimidinyl, pyrazolyl or thiophenyl, and $R^1$ may optionally be substituted with one or two $(C_1-C_3)$ alkyl moieties.

Other preferred compounds of this invention include those compounds of the formula Ib wherein $R^3$ is a group of the formula III, VII or IX; $R^2$ is hydrogen; the fused bicyclic ring system to which W and the $-CH_2NR^2R^3$ sidechain are attached is benzoxazolyl, benzisoxazolyl, benzthiazolyl, benzthiophenyl or benzimidazolyl; and W is $(C_1-C_6)$ alkoxy optionally substituted with from one to five fluorine atoms.

More preferred compounds of this invention are the foregoing preferred compounds wherein: (a) $R^3$ is a group of the formula III and $R^9$ is benzhydryl; (b) $R^3$ is a group of the formula VII, $R^{12}$ is phenyl, each of $R^{13}$, $R^{14}$, $R^{15}$ and $R^{16}$ is hydrogen, m is zero and X is $-(CH_2)_3-$; or (c) $R^3$ is a group of the formula IX, r is two and $R^{19}$ is benzhydryl.

Other more preferred compounds of this invention are those compounds of the formula Ia wherein: (a) $R^3$ is a group of the formula III wherein the substituents at positions "2" and "3" of the nitrogen containing ring are in the cis configuration, $R^9$ is benzhydryl and A is phenyl; or (b) $R^3$ is a group of the formula VII wherein $R^{12}$ and the substituent at position "3" of the nitrogen containing ring are in the cis configuration, A is phenyl, $R^{12}$ is phenyl, each of $R^2$, $R^{13}$, $R^{14}$, $R^{15}$ and $R^{16}$ is hydrogen, m is zero, W is methoxy or isopropoxy, X is $-(CH_2)_3-$ and $R^1$ is thiazolyl, imidazolyl, pyrrolyl, oxazolyl, pyridyl, pyrimidinyl, pyrazolyl, thiophenyl or thiadiazolyl.

Other more preferred compounds of this invention are those compounds of the formula Ib wherein $R^3$ is a group of the formula IX wherein the substituents at positions "2" and "3" of the nitrogen containing ring are in the cis configuration, $R^{19}$ is benzhydryl, r is two and the fused bicyclic ring system to which W and the $-CH_2NR^2R^3$ sidechain are attached is benzisoxazolyl or benzthiazolyl.

Especially preferred compounds of the formula Ib are those wherein $R^3$ is a group of the formula IX, $R^{19}$ is benzhydryl, the fused bicyclic ring system to which W and the —CH$_2$NR$^2$R$^3$ sidechain are attached is benzisoxazolyl, and W is methoxy.

Other especially preferred compounds of the formula Ib are those wherein R$^3$ is a group of the formula VII, R$^{12}$ is phenyl, each of R$^{13}$, R$^{14}$, R$^{15}$ and R$^{16}$ is hydrogen, m is zero, X is —(CH$_2$)$_3$—, and the fused bicyclic ring system to which W and the —CH$_2$NR$^2$R$^3$ sidechain are attached is benzothiazolyl, benzoxazolyl, benzthiophenyl or benzimidazolyl.

Especially preferred compounds of the formula Ia are those wherein R$^3$ is a group of the formula VII, each of R$^{13}$, R$^{14}$, R$^{15}$ and R$^{16}$ is hydrogen, m is zero, X is —(CH$_2$)$_3$—, A is phenyl, W is methoxy, and R$^1$ is selected from thiazolyl, imidazolyl, thiadiazolyl, pyridyl, pyrimidinyl, pyrazolyl, thiophenyl and isoxazolyl.

Specific preferred compounds of the formula I include the following:

(2S,3S)-3-[2-methoxy-5-(2-thiazolyl)benzyl]amino-2-phenylpiperidine;

(2S,3S)-3-[5-(2-imidazolyl)-2-methoxybenzyl]amino-2-phenylpiperidine;

(2S,3S)-3-[2-methoxy-5-(2-oxopyrrolidinyl)benzyl]amino-2-phenylpiperidine;

(2S,3S) -3-[2-methoxy-5-(4-methyl-2-thiazolyl)benzyl]-amino-2-phenylpiperidine;

(2S,3S)-3-[2-methoxy-5-(1,2,3-thiadiazol-4-yl)benzyl]-amino-2-phenylpiperidine;

(2S,3S)-(6-methoxy-2-methyl-benzothiazol-5-ylmethyl)-(2-phenylpiperidin-3-yl)amine;

(2S,3S)-[5-(2,5-dimethyl-pyrrol-1-yl) -2-methoxybenzyl] -(2-phenylpiperidin-3-yl)amine;

(2S,3S)-3-[2-methoxy-5-(5-oxazolyl)benzyl amino-2-phenylpiperidine;

(2S,3S)-(6-methoxy-2-phenyl-benzothiazol-5-ylmethyl)-(2-phenylpiperidin-3-yl)-amine;

(2S,3S)-(6-methoxy-2-cyclopropyl-benzothiazol-5-ylmethyl)-(2-phenylpiperidin-3-yl)amine;

(2S,3S)-(6-methoxy-2-tert-butyl-benzothiazol-5-ylmethyl)-(2-phenylpiperidin-3-yl)amine;

(2S,3S)-(6-isopropoxyoxy-2-phenyl-benzothiazol-5-ylmethyl)-(2-phenylpiperidin-3-yl)amine;

(2S,3S)-(6-isopropoxyoxy-2-methyl-benzothiazol-5-ylmethyl)-(2-phenylpiperidin-3-yl)amine;

(2S,3S)-(6-trifluoromethoxy-2-methyl-benzothiazol-5-ylmethyl)-(2-phenylpiperidin-3-yl)amine;

(2S,3S)-(6-methoxy-2-methyl-benzoxazol-5-ylmethyl)-(2-phenylpiperidin-3-yl)amine;

(1SR,2SR,3SR,4RS)-3-[6-methoxy-3-methylbenzisoxazol-5-yl]methylamino-2-benzhydrylazanorbornane;

(2S,3S)-(2-methoxy-5-pyridin-2-ylbenzyl)-(2-phenylpiperidin-3-yl)amine;

(2S,3S)-(2-methoxy-5-pyrimidin-2-ylbenzyl)-(2-phenylpiperidin-3-yl)amine;

(2S,3S)-(2-methoxy-5-pyridin-3-ylbenzyl)-(2-phenylpiperidin-3-yl)amine;

(2S,3S)-[2-methoxy-5-(6-methylpyridin-2-yl)benzyl]-(2-phenylpiperidin-3-yl)amine;

(2S,3S)-[5-(3,5-dimethylpyrazol-1-yl)-2-methoxybenzyl] -(2-phenylpiperidin-3-yl)amine;

(2S,3S)-[2-methoxy-5-(3,4,5-trimethylpyrazol-1-yl)benzyl]-(2-phenylpiperidin-3-yl)amine;

(2S,3S)-[2-isopropoxy-5-(3,4,5-trimethylpyrazol-1-yl)benzyl]-(2-phenylpiperidin-3-yl)amine;

(2S,3S)-[5-(3,5-diisopropylpyrazol-1-yl)-2-methoxybenzyl]-(2-phenylpiperidin-3-yl)amine;

(2S,3S)-[5-(3,5-dimethylthiophen-2-yl)-2-methoxybenzyl]-(2-phenylpiperidin-3-yl)amine; and (2S,3S)-(6-methoxy-2,3-dimethyl-benzo[b]thiophen-7-ylmethyl)-(2-phenylpiperidin-3-yl)amine.

Other compounds of the formula I include the following:

(2S,3S)-(6-methoxy-3-methyl-benzo[d]isoxazol-5-ylmethyl)-(2-phenylpiperidin-3-yl)-amine;

(1SR,2SR,3SR,4RS)-(2-benzhydryl-1-azabicyclo[2.2.1]hept-3-yl)-(6-methoxy-2-methyl-benzothiazol-5-ylmethyl)-amine;

(2S,3S)-(6-methoxy-benzoxazol-5-ylmethyl)-(2-phenylpiperidin-3-yl)-amine;

(2S,3S)-(6-methoxy-benzothiazol-5-ylmethyl)-(2-phenylpiperidin-3-yl)-amine;

(2S,3S)-5-methoxy-1-methyl-6-(2-phenylpiperidin-3-ylaminomethyl)-1,3-dihydro-indol-2-one;

(2S,3S)-6-methoxy-3-methyl-5-(2-phenylpiperidin-3-ylaminomethyl)-3H-benzoxazol-2-one;

(2S,3S)-6-methoxy-3-methyl-5-(2-phenylpiperidin-3-ylaminomethyl)-3H-benzothiazol-2-one;

(2S,3S)-5-methoxy-1,3-dimethyl-6-(2-phenylpiperidin-3-ylaminomethyl)-1,3-dihydro-benzoimidazol-2-one;

(2S,3S)-(6-methoxy-3-methyl-3H-benzotriazol-5-ylmethyl)-(2-phenylpiperidin-3-yl)amine;

(2S,3S)-(2-methoxy-5-[1,2,3]thiadiazol-4-yl-benzyl)-(2-phenyl-1-azabicyclo[2.2.2]oct-3-yl)amine;

(2S,3S)-(2-methoxy-5-[1,2,3]thiadiazol-4-yl-benzyl)-(2-benzhydryl-1-azabicyclo[2.2.2]oct-3-yl)amine;

(2S,3S)-(6-methoxy-2-methyl-benzothiazol-5-ylmethyl)-(2-phenyl-1-azabicyclo[2.2.2]oct-3-yl)amine;

(2S,3S)-(6-methoxy-2-methyl-benzothiazol-5-ylmethyl)-(2-benzhydryl-1-azabicyclo[2.2.2]oct-3-yl)amine;

(2S,3S)-(2-methoxy-5-thiazol-2-yl-benzyl)-(2-benzhydryl-1-azabicyclo[2.2.2]oct-3-yl)amine;

(2S,3S)-(6-methoxy-2-methyl-benzothiazol-5-ylmethyl)-(2-phenyl-1-azabicyclo[2.2.1]hept-3-yl)amine;

(2S,3S)-(6-methoxy-2-methyl-benzothiazol-5-ylmethyl)-(2-benzhydryl-1-azabicyclo[2.2.1]hept-3-yl)amine;

(2S,3S)-(2-methoxy-5-[1,2,4]triazol-4-yl-benzyl)-(2-phenylpiperidin-3-yl)amine;

(2S,3S)-(2-methoxy-5-[1,2,4]triazol-1-yl-benzyl)-(2-phenylpiperidin-3-yl)amine;

(2S,3S)-(2-methoxy-5-thiazol-2-ylbenzyl)-(2-phenyldecahydroquinolin-3-yl)amine;

(2S,3S)-(2-methoxy-5-thiazol-2-ylbenzyl)-(2-phenyloctahydro-indol-3-yl)amine;

(2S,3S)-(2-methoxy-5-oxazol-4-ylbenzyl)-(2-phenylpiperidin-3-yl)amine;

(2S,3S)-(6-methoxy-2-(2-propyl)-benzothiazol-5-ylmethyl)-(2-phenylpiperidin-3-yl)-amine;

(1SR,2SR,3SR,4RS)-(2-benzhydryl-1-azabicyclo[2.2.1]hept-3-yl)-(6-methoxy-2-phenylbenzothiazol-5-ylmethyl)amine;

(1SR,2SR,3SR,4RS)-(2-benzhydryl-1-azabicyclo[2.2.1]hept-3-yl)-(6-methoxy-2-cyclopropylbenzothiazol-5-ylmethyl)amine;

(1SR,2SR,3SR,4RS)-(2-benzhydryl-1-azabicyclo[2.2.1]hept-3-yl)-(6-methoxy-2-tert-butylbenzothiazol-5-ylmethyl)amine;

(1SR,2SR,3SR,4RS)-(2-benzhydryl-1-azabicyclo[2.2.1]hept-3-yl)-(6-methoxy-2-(2-propyl)benzothiazol-5-ylmethyl)amine;

(1SR, 2SR, 3SR, 4RS)-(2-benzhydryl-1-azabicyclo[2.2.1]hept-3-yl)-(6-isopropoxyoxy-2-phenylbenzothiazol-5-ylmethyl)amine;

(1SR,2SR,3SR, 4RS)-(2-benzhydryl-1-azabicyclo[2.2.1]hept-3-yl)-(6-isopropoxyoxy-2-methylbenzothiazol-5-ylmethyl)amine;

(1SR,2SR,3SR,4RS)-(2-benzhydryl-1-azabicyclo[2.2.1]hept-3-yl)-(6-trifluoromethoxy-2-methylbenzothiazol-5-ylmethyl)amine;

(6-methoxy-1-oxa-2,3-diazainden-5-ylmethyl)-(2-phenylpiperidin-3-yl)amine; and (6-methoxy-2-methyl-1H-benzoimidazol-5-ylmethyl)-(2-phenylpiperidine-3-yl)amine.

The present invention also relates to compounds of the formulae

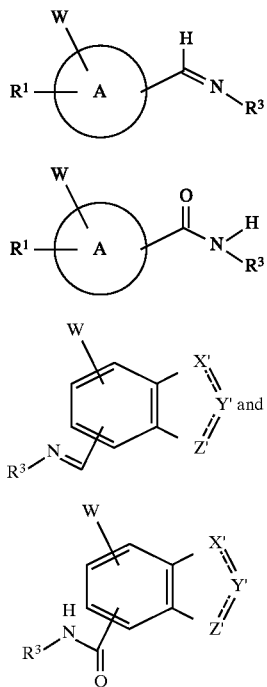

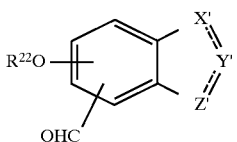

wherein ring A, $R^1$, $R^3$, W, X', Y' and Z' are defined as above. It also relates to compounds of the formula wherein X' is —S— or —O—, and each of Y' and Z' is, independently, =N—, =CH—, =C[(C$_1$–C$_6$)alkyl]— or =C(C$_6$H$_5$)—, wherein the alkyl moiety of said =C[(C$_1$–C$_6$)alkyl]— may optionally be substituted with from one to three fluorine atoms and the phenyl moiety of said =C(C$_6$H$_5$)— may optionally be substituted with from one to three substituents independently selected from halo and trifluoromethyl, with the proviso that Y' and Z' can not both be =N—, and $R^{22}$ is methyl, ethyl, n-propyl, isopropyl, t-butyl, trifluoromethyl, (C$_1$–C$_6$)alkyl, (C$_3$–C$_6$)cycloalkyl or benzyl. Compounds of the formulae XI, XII, XI-A, XII-A and XVIII are intermediates in the synthesis of compounds of the formulae Ia and Ib.

The present invention also relates to a pharmaceutical composition for treating or preventing a condition selected from the group consisting of inflammatory diseases (e.g., arthritis, psoriasis, asthma and inflammatory bowel disease), anxiety, depression or dysthymic disorders, urinary incontinence, gastrointestinal disorders such as emesis and colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in treating or preventing such condition, and a pharmaceutically acceptable carrier.

The present invention also relates to a method of treating or preventing a condition selected from the group consisting of inflammatory diseases (e.g., arthritis, psoriasis, asthma and inflammatory bowel disease), anxiety, depression or dysthymic disorders, urinary incontinence, gastrointestinal disorders such as emesis and colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in treating or preventing such condition.

The present invention also relates to a pharmaceutical composition for antagonizing the effects of substance P in a mammal, including a human, comprising a substance P antagonizing amount of a compound of the formula I, or a pharmaceutically acceptable salt thereof, and a pharmaceutically acceptable carrier.

The present invention also relates to a method of antagonizing the effects of substance P in a mammal, including a human, comprising administering to said mammal a substance P antagonizing amount of a compound of the formula I, or a pharmaceutically acceptable salt thereof.

The present invention also relates to a pharmaceutical composition for treating or preventing a disorder in a mammal, including a human, resulting from an excess of substance P, comprising a substance P antagonizing amount of a compound of the formula I, or a pharmaceutically acceptable salt thereof, and a pharmaceutically acceptable carrier.

The present invention also relates to a method of treating or preventing a disorder in a mammal, including a human, resulting from an excess of substance P, comprising administering to said mammal a substance P antagonizing amount of a compound of the formula I, or a pharmaceutically acceptable salt thereof.

The present invention also relates to a pharmaceutical composition for treating or preventing a condition selected from the group consisting of inflammatory diseases (e.g., arthritis, psoriasis, asthma and inflammatory bowel disease), anxiety, depression or dysthymic disorders, urinary incontinence, gastrointestinal disorders such as emesis and colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in antagonizing the effect of substance P at its receptor site, and a pharmaceutically acceptable carrier.

The present invention also relates to a method of treating or preventing a condition selected from the group consisting of inflammatory diseases (e.g., arthritis, psoriasis, asthma and inflammatory bowel disease), anxiety, depression or dysthymic disorders, urinary incontinence, gastrointestinal disorders such as emesis and colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in antagonizing the effect of substance P at its receptor site, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically. acceptable salt thereof, effective in treating or preventing such disorder, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in treating or preventing such disorder.

The compounds of the formula I have chiral centers and therefore exist in different enantiomeric forms. This invention relates to all optical isomers and all stereoisomers of compounds of the formula I, and mixtures thereof.

DETAILED DESCRIPTION OF THE INVENTION

The compounds of the formula I may be prepared as described in the following reaction schemes and discussion. Unless otherwise indicated, ring A, W, $R^1$, $R^2$, $R^3$, $R^4$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{22}$, X, Z, Y, X', Y', Z', m, n, o, p, q, r, x, y, and z, and structural formulas Ia, Ib, II, III, IV, V, VI, VII, VIII, IX, XI, XII, XI-A and XII-A in the reaction schemes and discussion that follow are defined as above.

As indicated above, compounds of the formulae Ia and Ib are referred to, collectively, as "compounds of the formula I".

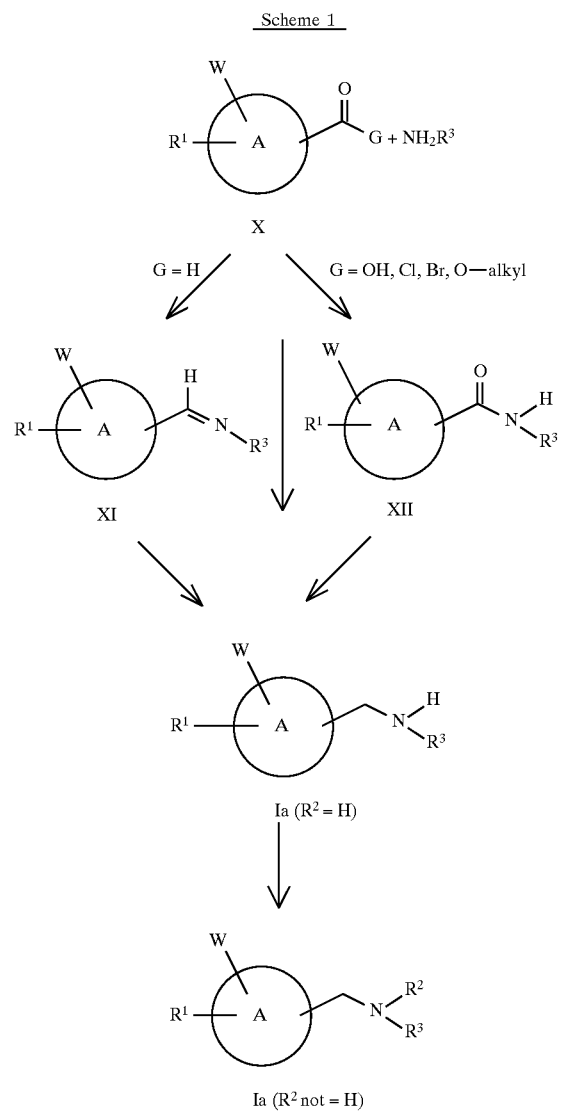

Scheme 2

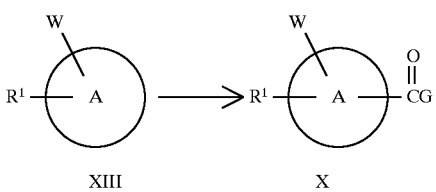

Scheme 3

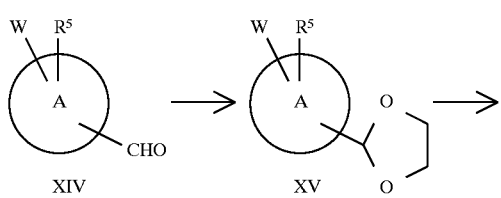

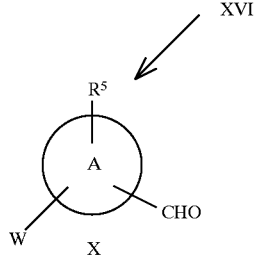

Scheme 4

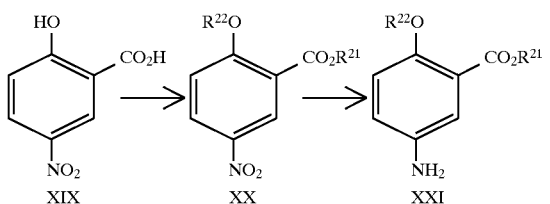

Scheme 4 -continued

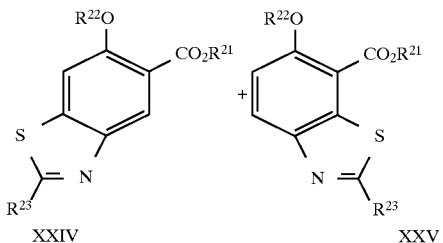

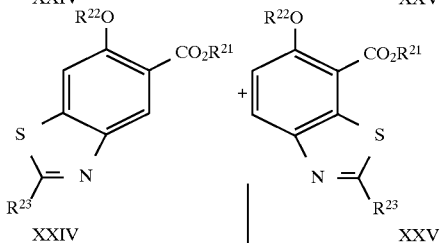

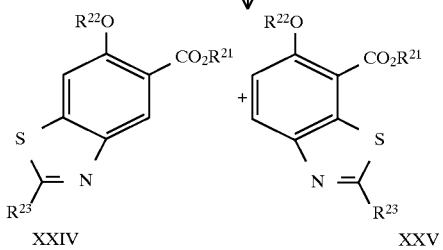

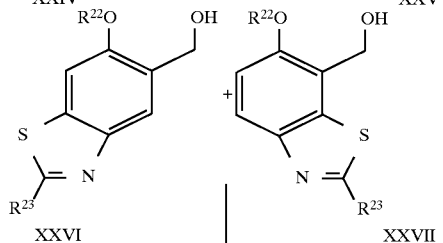

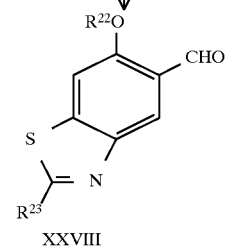

Scheme 1 illustrates the preparation of compounds of the formula Ia from starting materials of the formula X wherein G is hydrogen, hydroxy, chloro, bromo or ($C_1$–$C_6$) alkoxy.

Referring to scheme 1, a compound of the formula X wherein G is hydrogen may be converted directly into the corresponding compound of the formula I by reacting it with a compound of the formula $NH_2R^3$ in the presence of a reducing agent. Reducing agents that may be used include sodium cyanoborohydride, sodium triacetoxyborohydride, sodium borohydride, hydrogen and a metal catalyst, zinc and hydrochloric acid, and formic acid. This reaction is typically conducted in a reaction inert solvent at a temperature from about 0° C. to about 150° C. Suitable reaction inert solvents include lower alcohols (e.g., methanol, ethanol and isopropanol), 1,2-dichloroethane, acetic acid and tetrahydrofuran (THF). Preferably, the solvent is acetic acid, the temperature is about 25° C., the reducing agent is sodium triacetoxyborohydride, and the reaction is conducted in the presence of a dehydrating agent such as molecular sieves.

Alternatively, the reaction of a compound of the formula X with a compound of the formula $NH_2R^3$ may be carried out in the presence of a dehydrating agent or by using an apparatus designed to remove azeotropically the water generated, to produce an imine of the formula

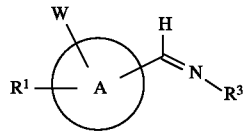

which is then reacted with a reducing agent as described above, preferably with sodium triacetoxyborohydride in an acetic acid or 1,2-dichloroethane solvent at about room temperature. The preparation of the imine XI is generally carried out in a reaction inert solvent such as benzene, xylene or toluene, preferably toluene, at a temperature from about 25° C. to about 110° C., preferably at about the reflux temperature of the solvent. Suitable dehydrating agents/solvent systems include titanium tetrachloride/dichloromethane, titanium isopropoxide/dichloromethane and molecular sieves. Titanium tetrachloride/dichloromethane is preferred.

Compounds of the formula X wherein G is hydroxy, chloro, bromo or $(C_1-C_6)$alkoxy may be converted into the corresponding compounds of formula XII having the desired $R^3$ group by reacting them with the appropriate compound of the formula $NH_2R^3$ under conditions that will be obvious to those skilled in the art, and then reducing the resulting amides to yield the desired compounds having formula I wherein $R^2$ is hydrogen. When G is hydroxy, the compound of formula X is reacted with $NH_2R^3$ in the presence of an activating agent. Appropriate activating agents include carbonyldiimidazole, chloroformates such as isobutyl chloroformate, diethylphosphoryl cyanide and dicyclohexylcarbodiimide. carbonyldiimidazole is preferred. This reaction is generally conducted at a temperature from about 0° C. to about 50° C., preferably at about 25° C., in an inert solvent such as chloroform, diethyl ether, THF or dimethylformamide (DMF).

When G is chloro or bromo, the reaction of the compound of formula X with the appropriate compound of formula $NH_2R^3$ is typically carried out in the presence of an acid scavenger in an aprotic solvent at a temperature from about 0° C. to about 100° C. Suitable acid scavengers include triethylamine (TEA), pyridine and inorganic salts such as sodium and potassium carbonate. Suitable solvents include methylene chloride ($CH_2Cl_2$), chloroform ($CHCl_3$), benzene, toluene and tetrahydrofuran (THF). Preferably, the reaction is conducted in $CH_2Cl_2$ at room temperature using TEA as the acid scavenger.

When G is O—$(C_1-C_6)$alkyl, the reaction of the compound of formula $NH_2R^3$ is usually conducted in an aprotic solvent such as benzene, toluene, chlorobenzene or xylenes, at a temperature from about 25° C. to about 100° C., preferably at about the reflux temperature of the solvent.

Reduction of the compound of formula XII so formed yields the corresponding compound of the formula I wherein $R^2$ is hydrogen. This is generally accomplished using a reducing agent such as lithium aluminum hydride, borane dimethylsulfide complex, borane-THF or diborane, in an aprotic solvent such as THF, dioxane or diethyl ether, at a temperature from about 0° C. to about 70° C. Preferably, the reducing agent is borane dimethylsulfide complex and the reaction is carried out at about room temperature in an ethereal solvent such as THF.

Compounds of the formula Ib may also be prepared by the procedures depicted in schemes 1 and 2 and described above, with the exception that ring system A in intermediate compounds X, XI and XII is replaced with the fused bicyclic ring system of the desired compound of formula Ib and $R^1$ is absent.

Compounds of the formula I wherein $R^2$ is hydrogen may be converted into the corresponding compounds wherein $R^2$ is —$CO_2(C_1-C_{10})$alkyl by reacting them with a $(C_1-C_{10})$ alkyl halocarbonate such as methyl or ethyl chloroformate in the presence of an acid scavenger. Typically, this reaction is conducted in an polar solvent such as chloroform, methylene chloride, water or a water/acetone mixture, at a temperature from about 0° C. to about 100° C., preferably at about room temperature. Suitable acid scavengers include triethylamine, pyridine and potassium and sodium carbonate or bicarbonate.

When $R^3$ is a group of the formula II, the starting materials of the formula $NH_2R^3$ may be prepared as described in U.S. Pat. No. 5,162,339, which issued on Nov. 11, 1992. This patent is incorporated herein in its entirety.

When $R^3$ is a group of the formula III, the starting materials of the formula $NH_2R^3$ may be prepared as described in U.S. patent application Ser. No. 532,525, filed Jun. 1, 1990 and PCT Patent Application PCT/US 91/02853, filed Apr. 25, 1991. Both these applications are incorporated herein in their entirety.

When $R^3$ is a group of the formula IV, V or VI, the starting materials of the formula $NH_2R^3$ may be prepared as described in U.S. patent application Ser. No. 557,442, filed Jul. 23, 1990 and PCT Patent Application PCT/US 91/03369, filed May 14, 1991. Both these applications are incorporated herein in their entirety.

When $R^3$ is a group of the formula VII, the starting materials of the formula $NH_2R^3$ may be prepared as described in U.S. patent application Ser. No. 724,268, filed Jul. 1, 1991, U.S. patent application Ser. No. 800,667, filed Nov. 27, 1991 and PCT Patent Application PCT/US 92/00065, filed Jan. 14, 1992. These applications are incorporated herein in their entirety.

When $R^3$ is a group of the formula VIII, the starting materials of the formula $NH_2R^3$ may be prepared as described in PCT Patent Application PCT/US 91/05776, filed Aug. 20, 1991, U.S. patent application Ser. No. 800, 667, filed Nov. 27, 1991 and PCT Patent Application PCT/US 92/00065, filed Jan. 14, 1992. These applications are incorporated herein in their entirety.

When $R^3$ is a group of the formula IX, the starting materials of the formula $NH_2R^3$ may be prepared as described in U.S. patent application Ser. No. 719,884, filed Jun. 21, 1991. This application is incorporated herein in its entirety.

Scheme 2 illustrates one method of preparing the starting materials of formula X wherein G is hydrogen. This is the preferred method of preparing compounds of the formula X wherein G is hydrogen and $R^1$ is thiazolyl, thiadiazolyl and oxazolyl. Once formed, these compounds can be converted into the corresponding compounds of the formula I or XI according to the procedures described above.

Referring to scheme 2, a compound of the formula XIII is reacted with titanium tetrachloride ($TiCl_4$) or tin tetrachloride ($SnCl_4$) and dichloromethyl methyl ether ($CHCl_2$—O—$CH_3$) at a temperature from about 0° C. to about room temperature, preferably at about 0° C., in a methylene chloride or tetrachloroethylene solvent to yield the corresponding aldehyde of formula X wherein G is hydrogen.

Alternatively, the compound of the formula XIII may be reacted with hexamethylene tetraamine and trifluoroacetic acid at a temperature from about 25° C. to about 80° C., preferably at about 70° C., to yield the same product.

Scheme 3 illustrates a preferred method of preparing compounds of the formula X wherein G is hydrogen and $R^1$ is a nitrogen containing heterocyclic group (e.g., a pyrrolyl, triazolyl or imidazolyl group). Referring to scheme 3, the —CHO group of a benzaldehyde of the formula XIV is protected by conversion to the corresponding 1,3-dioxolane of formula XV, wherein $R^5$ is a suitable leaving group such as iodine or bromine. This reaction is generally carried out by heating a mixture of the benzaldehyde and ethylene glycol in an inert solvent such as benzene or toluene, preferably in the presence of an acid catalyst such as p-toluenesulfonic acid, and preferably at the reflux temperature of the solvent to remove the water formed in the reaction.

The resulting compound of formula XV is then reacted with a heterocyclic compound of the formula $R^1H$ to form the corresponding compound of formula XVI. Typically, the reaction is carried out in an aprotic, nonpolar solvent such as xylene or toluene, or in the absence of a solvent (e.g., as a melt of imidazole and the compound of the formula XV) at a temperature from about 100° C. to about 300° C., in the presence of an inorganic metal catalyst such as copper metal or copper iodide, in a high pressure reactor at a pressure from about 1 atm to about 5 atm. Preferably, the reaction is carried out neat using a copper metal catalyst, at a temperature from about 140° C. to about 160° C. and at a pressure from about 2 atm to about 3 atm.

Treatment of the compound of formula XVI formed in the above reaction with a mixture of aqueous hydrochloric acid in acetone at a temperature from about 0° C. to about 50° C., preferably at room temperature, will convert the dioxolane to the desired compound of formula X.

Alternatively, compounds of the formula X wherein G is hydrogen and $R^1$ does not contain an ionizable proton (for example, $R^1$=2-pyridyl, 2-thienyl or 2-pyrimidinyl) can be prepared by reacting a compound of the formula XV, as depicted in scheme 3 and defined above, wherein $R^5$ is bromine or iodine, with magnesium metal to form a Grignard reagent of the formula

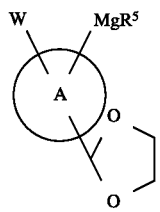

and then reacting the Grignard reagent in situ with a halogen substituted heterocyclic compound of the formula $X''R^1$ wherein $X''$ is chloro, bromo or iodo under standard Grignard conditions. These reactions are typically conducted in an ethereal solvent (e.g., diethyl ether or tetrahydrofuran), at a temperature from about 0° C. to about 70° C. They are preferably conducted at the reflux temperature of the solvent in the presence of a catalyst (e.g., tetrakis(triphenylphosphine) palladium (O)).

Compounds of the formula X wherein G is other than hydrogen can be prepared from commercially available sources by methods well known to those skilled in the art. For example, compounds of the formula X wherein G is hydroxy can be obtained by: (1) oxidizing the corresponding compounds of the formula

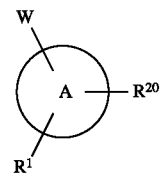

wherein $R^{20}$ is methyl with potassium permanganate in a reaction inert solvent such as acetone; (2) oxidizing an alcohol of the formula XVII wherein $R^{20}$ is hydroxymethyl with manganese dioxide; or (3) subjecting a compound of the formula XVII wherein $R^{20}$ is chloro, bromo or iodo to Grignard reaction conditions (i.e., reacting the compound of formula XVII with magnesium metal to form an intermediate of the formula

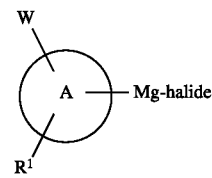

and then treating the intermediate with carbon dioxide.

The foregoing carboxylic acids of the formula X wherein G is hydroxy can be converted into the corresponding compounds of the formula X wherein G is chlorine or bromine by reaction with such reagents as sulfonyl chloride, phosphorus trichloride, phosphorus pentachloride and phosphorous tribromide.

Carboxylic esters of the formula X wherein G is ($C_1$–$C_6$) alkoxy can be prepared by a variety of methods known in the art. One such method involves reacting the corresponding acid halide in a ($C_1$–$C_6$)alkanol in the presence of a catalytic amount of hydrochloric, sulfuric or paratoluenesulfonic acid at a temperature from about room temperature to about the boiling point of the alcohol employed.

Compounds of the formula Ia wherein $R^1$ is pyrrolyl can also be prepared from the corresponding compounds wherein $R^1$ is replaced by an amino group. The corresponding amine may be obtained by reducing the corresponding nitro compound using one of several methods known to those skilled in the art. One such method involves catalytic hydrogenation of the nitro compound using hydrogen gas and a palladium on carbon catalyst in an inert solvent such as methanol or ethanol at about room temperature and a pressure of about 1–5 atm. The reduction can also be accomplished using a reducing agent such as borane/methyl sulfide in tetrahydrofuran at a temperature from about 25° C. to about 70° C., preferably at the reflux temperature of the solvent. The latter reduction method is exemplified in Example 45 of U.S. patent application Ser. No. 932,392, filed on Aug. 19, 1992. This application is incorporated herein by reference in its entirety.

The amine can then be converted into the desired compound of formula I by the procedure described in Example 9.

Scheme 4 illustrates a method of preparing compounds of the formula

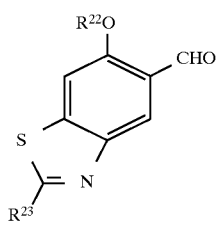

XXVIII wherein $R^{22}$ is methyl, ethyl, n-propyl, isopropyl, t-butyl, trifluoromethyl, $(C_1-C_6)$alkyl or benzyl, and $R^{23}$ is methyl, ethyl, propyl, isopropyl, t-butyl, trifluoromethyl, $(C_1-C_6)$ alkyl, benzyl or phenyl optionally substituted with from one to three substituents independently selected from halo, trifluoromethoxy, $(C_1-C_6)$ alkyl and $(C_1-C_6)$ alkoxy. These aldehydes are intermediates in the synthesis of compounds of the formula Ib wherein W is $OR^{22}$, X' is —S—, Y' is $CR^{23}$ and Z' is =N—. Such compounds of the formula Ib may be prepared from the foregoing aldehydes of formula XVIII as described above and depicted in scheme 1.

Referring to scheme 4, compounds of the formula XX may be prepared by direct alkylation of the corresponding phenols of the formula XIX using a common alkylating agent such as dimethyl sulfate, a methyl halide (e.g., methyl iodide), methyl triflate, methyl mesylate or methyl tosylate. The reaction is usually conducted in an inert solvent such as dimethyl formamide, N-methyl pyrrolidinone, tetrahydrofuran, methylene chloride or another similar solvent for a period of about 0.5 to 12 hours at a temperature of about 0° C. to the reflux temperature of the solvent. Typically, a base such as sodium hydride or potassium hydride is used, but other bases such as triethylamine, 1,8-diazobicyclo[5.4.0]undec-7-ene may be utilized as well. During the alkylation process, the carboxylic acid functionality of the phenol of formula XIX is also alkylated. However, various esterified derivatives of the compounds of formula XIX such as the methyl or ethyl ester (not shown in scheme 4) are also suitable starting materials for the foregoing transformation.

Reduction of the nitro functionality in the resulting compound of formula XX to yield the corresponding amine of formula XXI may be effected through hydrogenation with a noble metal catalyst such as platinum or palladium under a pressure of about 1–100 atmospheres of hydrogen gas in an inert solvent such as methanol, ethanol, ether, tetrahydrofuran or water (or a mixture of two or more such solvents). The reaction is most conveniently run at ambient temperature for about 0.5 to 12 hours. Alternatively, reduction of the nitro functionality may be carried out using a metal such as zinc or tin in a solvent such as acetic acid or water.

Formation of the amide of formula XXII is most conveniently conducted in an inert solvent such as methylene chloride, dichloroethane, tetrahydrofuran or toluene using one or more equivalents of an acylating agent such as acetic anhydride, acetyl chloride, benzoyl chloride, trimethylacetyl chloride, cyclopropyl carbonyl chloride or another alkyl or aryl acid chloride or anhydride. The reaction is most conveniently carried out in the presence of a base such as triethylamine or diisopropylamine or in aqueous solution under Schotten-Baumann conditions with sodium hydroxide. The reaction is generally conducted between about 0° C. and 60° C., with room temperature being preferred.

The thioamide of formula XXIII is formed from the corresponding amide of formula XXII by reacting the latter compound with a reagent such as 2,4-bis(4-methoxyphenyl)-1,3-dithia-2,4-diphosphetane-2,4-disulfide (Lawesson's Reagent) or phosphorous. pentasulfide in an inert solvent such as toluene, benzene, dichloroethane, dimethylformamide or hexamethylphosphorous triamide at a temperature from about room temperature to the reflux point of the solvent. The reaction may alternatively be run neat (without a solvent).

Cyclization of the thioamide of formula XXIII to form a mixture of regioisomeric benzothiazoles of the formulae XXIV and XXV is carried out by reacting the substrate with potassium ferricyanide in an aqueous base heated to about 50° C. for a period of about 1 to 12 hours. The mixture of regioisomers may be separated at this point or carried through to the end of the synthetic sequence.

Reduction of the mixture of compounds of the formulae XXIV and XXV or of the compound of formula XXIV alone can be conducted using a reducing agent such as lithium aluminum hydride, borane-THF, sodium bismethoxyethylaluminum hydride or a similar reducing agent in an inert solvent such as ether, tetrahydrofuran, dimethoxyethane or toluene. The reaction may be carried out at a temperature between about 0° C. and room temperature for a period of about 1 to 12 hours.

The resulting mixture of the regioisomeric alcohols of the formulae XXVI and XXVII (or XXVI separately) may be oxidized to form the desired aldehyde of formula XXVIII by reacting it with manganese dioxide in refluxing methylisobutyl ketone or another inert solvent for a period of about 1–12 hours. Alternatively, the oxidation can be carried out under "Swern" conditions (i.e., a mixture of dimethyl sulfoxide in methylene chloride with activation by oxalyl chloride or trifluoroacetic anhydride) or using other methods well known to those familiar with the art. Also effective are oxidizing agents such as pyridinium chlorochromate and pyridinium dichromate in an inert solvent such as methylene chloride, chloroform or dichloroethane.

The preparation of other compounds of the formula I not specifically described in the foregoing experimental section can be accomplished using combinations of the reactions described above that will be apparent to those skilled in the art.

In each of the reactions discussed or illustrated in schemes 1 to 4 above, pressure is not critical unless otherwise indicated. Pressures from about 0.5 atmospheres to about 5 atmospheres are generally acceptable, and ambient pressure, i.e. about 1 atmosphere, is preferred as a matter of convenience.

The novel compounds of the formula I and the pharmaceutically acceptable salts thereof are useful as substance P antagonists, i.e., they possess the ability to antagonize the effects of substance P at its receptor site in mammals, and therefore they are able to function as therapeutic agents in the treatment of the aforementioned disorders and diseases in an afflicted mammal.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the Formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

Those compounds of the formula I which are also acidic in nature, e.g., where $R^6$ or $R^{10}$ is carboxyphenyl, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compounds of formula I and their pharmaceutically acceptable salts exhibit substance P receptor-binding activity and therefore are of value in the treatment and prevention of a wide variety of clinical conditions the treatment or prevention of which are effected or facilitated by a decrease in substance P mediated neurotransmission. Such conditions include inflammatory diseases (e.g., arthritis, psoriasis, asthma and inflammatory bowel disease), anxiety, depression or dysthymic disorders, urinary incontinence, gastrointestinal disorders such as emesis and colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis. Hence, these compounds are readily adapted to therapeutic use as substance P antagonists for the control and/or treatment of any of the aforesaid clinical conditions in mammals, including humans.

The compounds of the formula I and the pharmaceutically acceptable salts thereof can be administered via either the oral, parenteral or topical routes. In general, these compounds are most desirably administered in dosages ranging from about 5.0 mg up to about 1500 mg per day, although variations will necessarily occur depending upon the weight and condition of the subject being treated and the particular route of administration chosen. However, a dosage level that is in the range of about 0.07 mg to about 21 mg per kg of body weight per day is most desirably employed. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The compounds of the formula I and their pharmaceutically acceptable salts ("the therapeutic compounds") may be administered alone or in combination with pharmaceutically acceptable carriers or diluents by either of the three routes. previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutic compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound of the present invention in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the therapeutic compounds of the present invention topically when treating inflammatory conditions of the skin and this may preferably be done by way of creams, jellies, gels, pastes, ointments and the like, in accordance with standard pharmaceutical practice.

The activity of the therapeutic compounds of the present invention as substance P receptor antagonists may be determined by their ability to inhibit the binding of substance P at its receptor sites in bovine caudate tissue, employing radioactive ligands to visualize the tachykinin receptors by means of autoradiography. The substance P antagonizing activity of the herein described compounds may be evaluated by using the standard assay procedure described by M. A. Cascieri et al., as reported in the *Journal of Biological Chemistry*, Vol. 258, p. 5158 (1983). This method essentially involves determining the concentration of the individual compound required to reduce by 50% the amount of radio-labelled substance P ligands at their receptor sites in said isolated cow tissues, thereby affording characteristic $IC_{50}$ values for each compound tested.

In this procedure, bovine caudate tissue is removed from a −70° C. freezer and homogenized in 50 volumes (w./v.) of an ice-cold 50 mM Tris (i.e., trimethamine which is 2-amino-2-hydroxymethyl-1,3-propanediol) hydrochloride buffer having a pH of 7.7. The homogenate is centrifuged at 30,000×G for a period of 20 minutes. The pellet is resuspended in 50 volumes of Tris buffer, rehomogenized and then recentrifuged at 30,000×G for another twenty-minute period. The pellet is then resuspended in 40 volumes of ice-cold 50 mM Tris buffer (pH 7.7) containing 2 mM of calcium chloride, 2 mM of magnesium chloride, 4 μg/ml of bacitracin, 4 μg/ml of leupeptin, 2 μg of chymostatin and 200 g/ml of bovine serum albumin. This step completes the production of the tissue preparation.

The radioligand binding procedure is then carried out in the following manner, viz., by initiating the reaction via the addition of 100 μl of the test compound made up to a concentration of 1 μM, followed by the addition of 100 μl of radioactive ligand made up to a final concentration 0.5 mM and then finally by the addition of 800 μl of the tissue preparation produced as described above. The final volume is thus 1.0 ml, and the reaction mixture is next vortexed and incubated at room temperature (ca. 20° C.) for a period of 20 minutes. The tubes are then filtered using a cell harvester, and the glass fiber filters (Whatman GF/B) are washed four times with 50 mM of Tris buffer (pH 7.7), with the filters having previously been presoaked for a period of two hours prior to the filtering procedure. Radioactivity is then determined in a Beta counter at 53% counting efficiency, and the $IC_{50}$ values are calculated by using standard statistical methods.

The ability of the therapeutic compounds of this invention to inhibit substance P induced effects in vivo may be determined by the following procedures "a" through "d". (Procedures "a" through "c" are described in Nagahisa et al., *European Journal of Pharmacology*, 217, 191–5 (1992), which is incorporated herein by reference in its entirety.)

a. Plasma extravasation in the skin

Plasma extravasation is induced by intradermal administration of substance P (50 μl, 0.01% BSA-saline solution) in dorsal skin of pentobarbital (25 mg/kg i.p.) anesthetized male Hartley guinea pigs weighing 450–500 g. The compound to be tested is dissolved in 0.1% methyl cellulose-water (MC) and dosed p.o. 1 hour before substance P challenge (3 pmol/site). Evans blue dye (30 mg/kg) is administered intravenously 5 minutes before challenge. After 10 minutes, the animals are sacrificed, the dorsal skin is removed, and the blue spots are punched out using a cork borer (11.5 mm oral dose (o.d.)). Tissue dye content is quantitated after overnight formamide extraction at 600 nm absorbance.

b. Capsaicin-induced plasma extravasation

Plasma extravasation is induced by intraperitoneal injection of capsaicin (10 ml of 30 μM solution in 0.1% BSA/saline) into pentobarbital anesthetized (25 mg/kg i.p.) guinea pigs. The compound to be tested is dissolved in 0.1% MC and dosed p.o. 1 hour before capsaicin challenge. Evans blue dye (30 mg/kg) is administered i.v. 5 minutes before challenge. After 10 minutes, the animals are sacrificed, and both right and left ureters are removed. Tissue dye content is quantitated as in "a" above.

C. Acetic acid-induced abdominal stretching

Male ddY mice (SLC, Japan), weighing 14–18 g, were fasted overnight. The compound to be tested is dissolved in 0.1% MC and dosed p.o. 0.5 hour before acetic acid (AA) injection (0.7%, 0.16 ml/10 g body weight). The animals are placed in clear beakers (1 per beaker) and the stretching response is counted 10 to 20 minutes after the AA injection (10 minute interval).

d. Substance P-induced hyperlocomotor paradigm

The anti-psychotic activity of the therapeutic compounds of the present invention as neuroleptic agents for the control of various psychotic disorders may be determined by a study of their ability to suppress substance P-induced or substance P agonist induced hypermotility in guinea pigs. This study is carried out by first dosing the guinea pigs with a control compound or with an appropriate test compound of the present invention, then injecting the guinea pigs with substance P or a substance P agonist by intracerebral administration via canula and thereafter measuring their individual locomotor response to said stimulus.

The present invention is illustrated by the following examples. It will be understood, however, that the invention is not limited to the specific details of these examples.

Preparation 1

2-Methoxy-5-(1,2,3-thiadiazol-4-yl)benzaldehyde

A mixture of 0.99 grams (5.15 mmol) of 4-(4-methoxyphenyl)-1,2,3-thiadiazole (Maybridge Chemical Co.) in 23 mL of anhydrous methylene chloride ($CH_2Cl_2$) cooled to 0° C., was treated with 2.3 mL (21.9 mmol) of titanium tetrachloride and stirred for 30 min. The red solution was treated with 0.97 mL (10.7 mmol) of α,α-dichloromethyl methyl ether and allowed to warm to room temperature overnight. The reaction mixture was then poured over 100 mL of saturated aqueous sodium bicarbonate ($NaHCO_3$), the pH was adjusted to 7–8 with solid $NaHCO_3$ and the solution was then extracted with $CH_2Cl_2$. The organic layer was dried with magnesium sulfate ($MgSO_4$) and concentrated to a yellow solid. Chromatography on silica gel (20% EtOAc: 80% Hexane) gave the pure title compound as a light yellow solid, 0.35 g (31%).

M.P. 156°–157° C.

$^1$H NMR (DMSO-$d_6$) δ 4.0 (s, 3H), 7.4 (d, 1H), 8.4 (m, 2H), 9.7 (s, 1H), 10.4 (s, 1H).

In the same manner, the following aldehyde intermediates were prepared:

2-Methoxy-5-(2-thiazolyl)benzaldehyde, 36%

M.P. 119°–120° C.

$^1$H NMR (CDCl$_3$) δ 4.0 (s, 3H), 7.1 (d, 1H), 7.3 (d, 1H), 7.8 (d, 1H), 8.2 (dd, 1H), 8.3 (d, 1H), 10.5 (s, 1H).

2-Methoxy-5-(4-methyl-2-thiazolyl)benzaldehyde, 35%, oil $^1$H NMR (CDCl$_3$) δ 2.46 (s, 3H), 3.95 (s, 3H), 6.82 (s, 1H), 7.02 (d, J=8.7 Hz, 1H), 8.15 (dd, 1H), 8.26 (d, J=2.4 Hz, 1H), 10.46 (s, 1H).

2-Methoxy-5-(5-oxazolyl)benzaldehyde, 22%

$^1$H NMR (CDCl$_3$) δ 4.0 (s, 3H), 7.1 (d, 1H), 7.4 (s, 1H), 7.8 (dd, 1H), 7.9 (s, 1H), 8.1 (d, 1H), 10.5 (s, 1H).

2-Methoxy-5-(6-methylpyridin-2-yl)benzoaldehyde $^1$H NMR (CDCl$_3$, free base) δ 2.6 (s, 3H), 3.95 (s, 3H), 7.0 (m, 2H), 7.4 (d, 1H), 7.6 (d, 1H), 8.3 (dd, 1H), 8.5 (d, 1H), 10.5 (s, 1H).

Mass Spectrum (m/e, %): 228 (M$^{+1}$), 227 (M+, 40), 85 (100).

2-Methoxy-5-(pyridin-2-yl)benzaldehyde $^1$H NMR (CDCl$_3$, free base) δ 4.0 (s, 3H), 7.1 (d, 1H), 7.2 (q, 1H), 7.7 (d, 2H), 8.3 (dd, 1H), 8.4 (d, 1H), 8.7 (d, 1H), 10.5 (s, 1H).

2-Methoxy-5-(pyridin-3-yl)benzaldehyde

M.p. 77°–79° C.

$^1$H NMR (CDCl$_3$, free base) δ 4.0 (s, 3H), 7.2 (d, 1H), 7.4 (m, 1H), 7.8 (dd, 1H), 7.9 (dd, 1H), 8.1 (d, 1H), 8.6 (dd, 1H), 8.9 (d, 1H), 10.5 (s, 1H).

2-Methoxy-5-(Pyrimidin-2-yl)benzaldehyde $^1$H NMR (CDCl$_3$, free base) δ 4.0 (s, 3H), 7.1 (d, 1H), 7.2 (t, 1H), 8.7 (d, 1H), 8.8 (d, 2H), 9.0 (d, 1H), 10.5 (s, 1H).

Mass Spectrum (m/e, %): 215 (M$^{+1}$, 100), 214 (M+, 35).

2-Methoxy-5-(3,5-dimethylpyrazol-1-yl) benzaldehyde $^1$H NMR (CDCl$_3$, free base) δ 2.4 (s, 6H), 4.0 (s, 3H), 6.0 (s, 1H), 7.05 (d, 1H), 7.6 (dd, 1H), 7.85 (d, 1H), 10.5 (s, 1H).

Mass Spectrum (m/e, %): 231 (M$^{+1}$, 100).

2-Methoxy-5-(3,4,5-trimethylpyrazol-1-yl)benzaldehyde

M.p. 115°–117° C.

$^1$H NMR (CDCl$_3$, free base) δ 1.9 (s, 3H), 2.1 (d, 6H), 4.0 (s, 3H), 7.0 (d, 1H), 7.8 (m, 1H), 7.9 (d, 1H), 10.5 (s, 1H).

Mass Spectrum (m/e, %): 245 (M$^{+1}$, 100).

2-Isopropoxy-5-(3,4,5-trimethylpyrazol-1-yl)benzaldehyde $^1$H NMR (CDCl$_3$, free base) δ 1.4 (d, 6H), 2.0 (s, 3H), 2.17 (s, 3H), 2.2 (s, 3H), 4.70 (m, 1H), 7.05 (d, 1H), 7.6 (dd, 1H), 7.8 (d, 1H), 10.5 (s, 1H).

2-Methoxy-5-(3,5-diisopropylpyrazol-1-yl)benzaldehyde $^1$H NMR (CDCl$_3$, free base) δ 1.2 (d, 6H), 1.3 (d, 6H), 3.0 (m, 2H), 4.0 (s, 3H), 6.1 (s, 1H), 7.0 (d, 1H), 7.6 (dd, 1H), 7.9 (d, 1H), 10.5 (s, 1H).

Mass Spectrum (m/e, %): 286 (m+, 75), 271 (100).

5-(3,5-Dimethylthiophen-2-yl)-2-methoxybenzaldehyde $^1$H NMR (CDCl$_3$, free base) δ 2.25 (s, 3H), 2.5 (s, 3H), 3.9 (s, 3H), 6.9 (d, 1H), 7.15 (d, 1H), 7.25 (m, 2H), 9.8 (s, 1H).

Mass Spectrum (m/e, %): 246 (M+, 100), 231 (35).

6-Methoxy-2,3-dimethyl-benzo[b]thiophene-7-carboxaldehyde

M.p. 155°–160°.

$^1$H NMR (CDCl$_3$, free base) δ 2.2 (s, 3H), 2.45 (s, 3H), 4.0 (s, 3H), 7.0 (d, 1H), 7.8 (d, 1H), 10.7 (s, 1H).

Mass Spectrum (m/e, %): 221 (M$^{+1}$, 100).

6-Methoxy-2-methyl-benzoxazol-5-ylaldehyde

6-Methoxy-2-methyl-benzoxazole (1.06 grams, 6.5 mmol) was taken up in 65 mL of dry methylene chloride and cooled to 0° C. Titanium tetrachloride (10.11 grams, 53.3 mmol) was added via syringe and the deep red solution was stirred for 30 min. Dichloromethyl methyl ether (4.63 grams, 40.3 mmol) was added dropwise and the reaction mixture darkened to a brown color. The reaction mixture was allowed to warm to room temperature and was stirred for 18 hours. The mixture was quenched into ice and water. The slurry was basified with aqueous saturated bicarbonate and extracted with methylene chloride. The organic phase was washed with saturated aqueous brine and then dried and evaporated in vacuo. The residue was chromatographed on silica eluting over a gradient of 20% ethyl acetate/hexanes to 50% ethyl acetate/hexanes. In addition to starting material, a more polar material, the desire aldehyde, was obtained in 69 mg. Further elutions led to the isolation of a regioisomeric aldehyde. The desired material displayed the following spectral data.

$^1$H NMR (250 MHz, CDCl$_3$) δ 10.48 (s, lH), 8.10 (s, 1H), 7.06 (s, lH), 3.98 (s, 3H), 2.62 (s, 3H).

Preparation 2

6-Methoxy-2-methyl-benzothiazol-5-ylaldehyde

6-Methoxy-2-methyl-benzothiazole [3.34 grams (18.63 mmol)] was taken up in 35 mL of trifluoroacetic acid and treated with 2.62 grams (18.63 mmol) of hexamethylenetetramine. The reaction was heated under reflux for seven hours. The reaction mixture was allowed to cool and was evaporated in vacuo. The residue was diluted with 200 mL of ethyl acetate and treated with 100 mL of saturated sodium bicarbonate solution. The organic phase was washed with saturated brine solution and was dried and evaporated. The residue was chromatographed on silica gel (elution with 20% ethyl acetate in hexanes) to provide 3.04 grams of recovered starting material and 10 mg of the desired aldehyde.

$^1$H NMR (250 MHz, CDCl$_3$) δ 10.52 (s, 1H), 8.36 (s, 1H), 7.38 (s, 1H), 3.99 (s, 3H), 2.82 (s, 3H).

In a similar manner, the following aldehyde intermediate was prepared.

6-Methoxy-3-methyl-benzo[d]isoxazol-5-ylaldehyde

6-Methoxy-3-methyl-benzo[d]isoxazole (1.4 g, 8.58 mmol) was taken up in 200 mL of trifluoroacetic acid and treated with 1.20 grams (8.6 mmol) of hexamethylenetetramine. The reaction was heated under reflux for 24 hours. The reaction mixture was allowed to cool and was evaporated in vacuo. The residue was diluted with 200 mL of methylene chloride and treated with 200 mL of saturated sodium bicarbonate solution. The organic phase was washed with saturated brine solution and was dried and evaporated. The residue was chromatographed on silica gel (elution with 15% ethyl acetate in hexanes) to provide 122.6 mg of the desired aldehyde.

$^1$H NMR (250 MHz, CDCl$_3$) δ 10.46 (s, 1H), 8.15 (s, 1H), 7.04 (s, 1H), 4.02 (s, 3H), 2.56 (s, 3H).

Preparation 3

5-(2-Imidazolyl)-2-methoxybenzaldehyde

To a solution of 2.04 grams (8.72 mmol) of 4-iodoanisole in 36 mL of CH$_2$Cl$_2$, cooled to 0° C., was added dropwise 2.0 mL (18.7 mmol) of titanium tetrachloride. After stirring for 30 min., 0.93 mL (10.3 mmol) of α,α-dichloromethyl methyl ether was added and the reaction maintained at 0° C. for another 2 hours. The reaction mixture was then poured with stirring into a mixture of 50 mL of CH$_2$Cl$_2$ and 50 mL of saturated aqueous sodium bicarbonate (NaHCO$_3$). After 30 min., this was filtered through diatomaceous earth, the organic layer was separated, the aqueous layer was twice extracted with CH$_2$Cl$_2$, and all of the organic layers were combined, dried with MgSO$_4$ and concentrated in vacuo. The crude residue was recrystallized from ethanol (EtOH) to give 5-iodo-2-methoxybenzaldehyde as pale yellow needles, 1.37 grams (60%).

$^1$H NMR (CDCl$_3$) δ 4.0 (s, 3H), 6.8 (d, 1H), 7.8 (dd, 1H), 8.1 (d, 1H), 10.4 (s, 1H).

A solution of 1.0 grams (3.82 mmol) of the above aldehyde, 0.85 mL of ethylene glycol, 20 mg of p-toluenesulfonic acid and 42 mL of toluene was refluxed under nitrogen for 18 hours, cooled and concentrated in vacuo. The residue was redissolved in 50 mL of $CH_2Cl_2$, washed with saturated aqueous $NaHCO_3$, dried over $MgSO_4$ and concentrated to an oil. Chromatography on silica gel (10% ethyl acetate (EtOAc): 90% hexane) gave 2-(5-iodo-2-methoxyphenyl)-1,3-dioxolane as a clear oil, 0.68 grams (58%).

$^1$H NMR ($CDCl_3$) δ 3.9 (s, 3H), 4.0–4.3 (m, 4H), 6.1 (s, 1H), 6.7 (d, 1H), 7.4 (dd, 1H), 7.9 (d, 1H).

In a Pyrex high pressure reaction tube, a solution of the preceding dioxolane (200 mg, 0.66 mmol), 140 mg (2.06 mmol) of imidazole and 90 mg (1.4 mmol) of copper powder in 1 mL of anhydrous tetrahydrofuran (THF) was stirred until homogeneous. The solvent was then evaporated under nitrogen, and the tube was sealed and heated in an oil bath at 140° C. for 16 hours. After cooling, the residue was dissolved in 20 mL of THF, filtered through a pad of diatomaceous earth and concentrated in vacuo to an oil. Chromatography on silica gel (100% ethyl acetate (EtOAc)) gave 60 mg of 2-(5-(2-imidazolyl)-2-methoxyphenyl)-1,3-dioxolane as a yellow oil.

MS: m/e 246 (m+).

The preceding oil in 20 mL of acetone was treated with 10 mL of 1N-hydrochloric acid (HCl) and stirred at 25° C. for 3 hours, evaporated in vacuo and extracted into $CH_2Cl_2$. After washing with water, the organic layer was dried over $MgSO_4$ and concentrated to a clear oil. Chromatography on silica gel (3% $CH_3OH$: 97% $CH_2Cl_2$) gave 5-(2-imidazolyl)-2-methoxybenzaldehyde as a clear oil, 30 mg (61%).

$^1$H NMR ($CDCl_3$) δ 4.0 (s, 3H), 7.1 (d, 1H), 7.1–7.3 (m, 2H), 7.6 (dd, 1H), 7.8 (d, 2H), 10.5 (s, 1H).

EXAMPLE 1

(2S,3S-3-[5-(2-Imidazolyl)-2-methoxybenzyl]amino-2-phenylpiperdine trihydrochloride dihydrate Under a nitrogen atmosphere, a mixture of 30 mg (0.15 mmol) of 5-(2-imidazolyl)-2-methoxybenzaldehyde and 54 mg (0.15 mmol) of (+)-(2S,3S)-3-amino-2-phenylpiperidine in 5 mL of dry toluene was stirred and heated to reflux for 18 hours, using a Dean-Stark trap. The toluene in the reaction flask was removed in vacuo, the residue was dissolved in 5 mL of anhydrous 1,2-dichloroethane and stirred for 10 min. Sodium triacetoxyborohydride (92 mg, 0.43 mmol) was added and stirring was continued overnight. The solvent was removed in vacuo and the residue was treated with 5 mL of water ($H_2O$) and extracted with methylene chloride ($CH_2Cl_2$) (3×10 mL). The organic extracts were combined, dried over magnesium sulfate ($MgSO_4$) and concentrated to an oil. Chromatography on silica gel using methylene chloride ($CH_2Cl_2$): Methanol ($CH_3OH$): concentrated ammonium hydroxide ($NH_4OH$) in a ratio of 94:5:1 gave the pure free base as a clear oil. The oil dissolved in $CH_2Cl_2$ was treated with a solution of $Et_2O$ saturated with hydrogen chloride (HCl) gas to give the title product as a pale yellow solid, 15.7 mg (21%).

M.P. 235° C. (decomp.)

$^1$H NMR ($CDCl_3$, free base) δ 1.5 (m, 1H), 1.7 (m, 1H), 1.9 (m, 4H), 2.2 (m, 1H), 2.9 (m, 2H), 3.3 (m, 1H), 3.5 (d, 1H), 3.6 (s, 3H), 3.7 (d, 1H), 3.9 (d, 1H), 6.7 (d, 1H), 7.0 (d, 1H), 7.1–7.4 (m, 8H), 7.7 (s, 1H).

FAB MS: m/e 363 (m+1)

Anal. calc'd for $C_{22}H_{26}N_4O.3HCl.2H_2O$: C, 52.03; H, 6.55; N, 11.03. Found: C, 51.84; H, 6.36; N, 10.53.

The title compounds of Examples 2 through 15 were prepared from (+)-(2S,3S)-3-amino-2-phenylpiperidine and the appropriate aldehyde using a procedure similar to that of Example 1.

EXAMPLE 2

(2S,3S)-3-[2-Methoxy-5-(2-thiazolyl)benzyl]amino-2-phenylpiperidine trihydrochloride dihydrate M.P. 207° C. (decomp.)

$^1$H NMR ($CDCl_3$, free base) δ 1.5 (m, 1H), 1.7 (m, 1H), 2.0 (m, 4H), 2.8 (m, 1H), 2.8 (m, 2H), 3.3 (m, 1H), 3.4 (d, 1H), 3.5 (s, 3H), 3.8 (d, 1H), 3.9 (d, 1H), 6.7 (d, 1H), 7.3 (m, 7H), 7.6 (d, 1H), 7.8 (m, 2H).

FAB MS: m/e 380 (m+1)

Anal. calc'd for $C_{22}H_{25}N_3OS.3HCl.2H_2O$: C, 50.34; H, 6.14; N, 8.00. Found: C, 50.24; H, 6.05; N, 7.84.

EXAMPLE 3

(2S,3S)-3-[2-Methoxy-5-(1,2,3-thiadiazol-4-yl)benzyl]amino-2-phenylpiperidine trihydrochloride dihydrate M.P. >270° C. (decomp.)

$^1$H NMR ($CDCl_3$, free base) δ 1.4 (m, 1H), 1.6 (m, 1H), 1.9 (m, 3H), 2.2 (m, 2H), 3.2 (m, 2H), 3.5 (d, 4H), 3.7 (d, 1H), 3.9 (d, 1H), 6.7 (d, 1H), 7.3 (m, 5H), 7.6 (d, 1H), 7.9 (dd, 1H), 8.4 (s, 1H).

FAB MS: m/e 381 (m+1, 100%), 353, 321.

EXAMPLE 4

(2S ,3S)-3-[2-methoxy-5-(5-oxazolyl)benzyl]amino-2-phenylpiperidine dihydrochloride M.P. 267° C. (decomp.)

$^1$H NMR ($CDCl_3$, free base) δ 1.5 (m, 1H), 1.7 (m, 1H), 2.0 (m, 4H), 2.2 (m, 1H), 2.9 (m, 2H), 3.3 (m, 1H), 3.5 (d, 1H), 3.6 (s, 3H), 3.7 (d, 1H), 3.9 (d, 1H), 6.7 (d, 1H), 7.2 (s, 1H), 7.3 (m, 6H), 7.5 (dd, 1H), 7.9 (s, 1H).

FAB MS: m/e 364 (m+1)

Anal. calc'd for $C_{22}H_{25}N_3O_2.2HCl$: C, 60.55; H, 6.24; N, 9.63. Found: C, 60.48; H, 6.21; N, 9.86.

EXAMPLE 5

(2S,3S)-3-[2-Methoxy-5-(4-methyl-2-thiazolyl)benzyl]amino-2-phenylpiperidine trihydrochloride M.P. 239° C. (decomp.)

$^1$H NMR ($CDCl_3$, free base) δ 1.5 (m, 1H), 1.7 (m, 1H), 2.2 (m, 1H) , 2.6 (s, 3H) , 2.9 (m, 2H) , 3.3 (m, 1H) , 3.4 (d, 1H), 3.5 (s, 3H), 3.6 (d, 1H), 3.8 (d, 1H), 6.7 (d, 1H), 6.8 (s, 1H), 7.2–7.4 (m, 5H), 7.6 (d, 1H), 7.8 (dd, 1H).

FAB MS: m/e 394 (m+1).

EXAMPLE 6

(2S,3S)-(2-Methoxy-5-pyridin-2-ylbenzyl)-(2-phenylpiperidin-3-yl)amine trihydrochloride hydrate M.p. 230° C.

$^1$H NMR ($CDCl_3$, free base) δ 1.35–2.2 (m, 6H), 2.8 (m, 2H), 3.3 (m, 1H), 3.5 (s, 3H), 3.6 (d, 1H), 3.8 (d, 1H), 3.9 (d, 1H), 6.7 (d, 1H), 7.0–7.3 (m, 6H), 7.5 (d, 1H), 7.6 (m, 2H), 7.8 (dd, 1H), 8.6 (M+1, 100).

Mass Spectrum (m/e, %): 374 (M+1, 100).

Anal. calc'd for $C_{24}H_{27}N_3O.3HCl.1/4H_2O$: C, 58.69; H, 6.21; N, 8.56. Found: C, 58.60; H, 6.18; N. 8.37.

EXAMPLE 7

(2S,3S)-(2-Methoxy-5-pyrimidin-2-ylbenzyl)-(2-phenylpiperidin-3-yl)amine dihydrochloride hydrate M.p. 207° C. (dec.)

¹H NMR (CDCl₃, free base) δ 1.5–2.0 (m, 5H), 2.4 (m, 1H), 2.8 (m, 1H), 2.8 (m, 2H), 3.4 (m, 1H), 3.5 (s, 3H), 3.6 (d, 1H), 3.9 (d, 1H), 4.0 (d, 1H), 5.7 (d, 1H), 7.1 (t, 1H), 7.4 (m, 5H), 8.1 (d, 1H), 8.3 (dd, 1H), 8.7 (d, 2H).

Mass Spectrum (m/e, %): 375 (M+1, 100).

Anal. calc'd for $C_{23}H_{26}N_4O \cdot 2HCl \cdot 2H_2O$: C, 57.14; H, 6.67; N, 11.59. Found: C, 57.23; H, 6.50; N, 11.44.

EXAMPLE 8

(2S,3S)-(2-Methoxy-5-pyridin-3-ylbenzyl)-(2-phenylpiperidin-3-yl)amine trihydrochloride hydrate M.p. 241° C. (dec.)

¹H NMR (CDCl₃, free base) δ 1.35–2.20 (m, 6H), 2.8 (m, 2H), 3.3 (d, 1H), 3.5 (d, 1H), 3.55 (s, 3H), 3.75 (d, 1H), 3.9 (d, 1H), 6.8 (d, 1H), 7.15–7.40 (m, 8H), 7.75 (m, 1H), 8.5 (dd, 1H), 8.72 (d, 1H).

Mass Spectrum (m/e, %): 374 (M+1, 100).

Anal. calc'd for $C_{24}H_{27}N_3O \cdot 3HCl \cdot H_2O$: C, 57.55; H, 6.44; N, 8.39. Found: C, 57.88; H, 6.67; N, 8.07.

EXAMPLE 9

(2S,3S)-[2-Methoxy-5-(6-methylpyridin-2-yl)benzyl]-(2-phenylpiperidin-3-yl)amine dihydrochloride hydrate M.p. 215°–220° C.

¹H NMR (CDCl₃, free base) δ 1.35–2.25 (m, 6H), 2.65 (s, 3H), 2.85 (m, 2H), 3.3 (d, 1H), 3.5 (s, 3H), 3.55 (d, 1H), 3.8 (d, 1H), 3.95 (d, 1H), 6.8 (d, 1H), 7.00 (d, 1H), 7.3 (m, 5H), 7.45 (d, 1H), 7.6 (m, 2H), 7.9 (dd, 1H).

Mass Spectrum (m/e, %): 387 (M+, 5), 268, 213 (100).

Anal. calc'd for $C_{25}H_{29}N_3O \cdot 2HCl \cdot 1/4H_2O$: C, 65.58; H, 6.83; N, 9.04. Found: C, 64.80; H, 6.76; N, 8.95.

EXAMPLE 10

(2S,3S)-[5-(3,5-Dimethylpyrazol-1-yl)-2-methoxybenzl]-(2-phenylpiperidin-3-yl)amine dihydrochloride hydrate M.p. 255°–259° C.

¹H NMR (CDCl₃, free base) δ 1.4–2.2 (m, 5H), 2.15 (d, 1H), 2.2 (s, 3H), 2.3 (s, 3H), 2.8 (m, 2H), 3.25 (d, 1H), 3.45 (d, 1H), 3.5 (s, 3H), 3.75 (d, 1H), 3.9 (d, 1H), 6.0 (s, 1H), 6.7 (d, 1H), 7.05 (d, 1H), 7.15–7.35 (m, 6H).

Mass Spectrum (m/e, %): 391 (M+1, 100), 232 (20).

Anal. calc'd for $C_{24}H_{30}N_4O \cdot 2HCl \cdot 1/4H_2O$: C, 61.60; H, 7.00; N, 11.97. Found: C, 61.60; H, 6.97; N, 11.72.

EXAMPLE 11

(2S,3S)-[2-Methoxy-5-(3,4,5-trimethylpyrazol-1-yl)benzyl]-(2-phenylpiperidin-3-yl)amine trihydrochloride M.p. 220°–225° C.

¹H NMR (CDCl₃, free base) δ 1.4 (d, 1H), 1.55 (tt, 1H), 1.95 (m, 3H), 2.05 (s, 3H), 2.15 (s+m, 4H), 2.25 (s, 3H), 2.8 (m, 2H), 3.3 (d, 1H), 3.45 (d, 1H), 3.5 (s, 3H), 3.75 (d, 1H), 3.9 (d, 1H), 6.7 (d, 1H), 7.0 (d, 1H), 7.15–7.35 (m, 6H).

Mass Spectrum (m/e, %): 406 (M+2, 100).

Anal. calc'd for $C_{25}H_{32}N_4O \cdot 3HCl \cdot 1/2CH_2Cl_2$: C, 55.04; H, 6.52; N, 10.07. Found: C, 54.80; H, 6.82; N, 9.74.

EXAMPLE 12

(2S,3S)-[2-Isopropoxy-5-(3,4,5-trimethylpyrazol-1-yl)benzyl]-(2-phenyl-piperidin-3-yl)amine hydrochloride hydrate M.p. 140°–155° C.

¹H NMR (CDCl₃, free base) δ 1.05 (dd, 6H), 1. 45–2.0 (m, 6H), 2.05 (s, 3H), 2.15 (s, 3H), 2.25 (s, 3H), 2.80 (t, 1H), 2.9 (d, 1H), 3.3 (d, 1H), 3.4 (d, 1H), 3.65 (d, 1H), 3.9 (d, 1H), 4.4 (m, 1H), 6.75 (d, 1H), 7.0 (d, 1H), 7.1–7.35 (m, 6H).

Mass Spectrum (m/e, %): 433 (M+1, 100).

Anal. calc'd for $C_{27}H_{36}N_4O \cdot HCl \cdot H_2O$: C, 66.58; H, 8.07; N, 11.50. Found: C, 66.54; H, 8.05; N, 11.83.

EXAMPLE 13

(2S,3S)-[5-(3,5-Diisopropylpyrazol-1-yl)-2-methoxybenzyl]-(2-phenylpiperidin-3-yl) amine dihydrochloride hydrate M.p. 222° C. dec.

¹H NMR (CDCl₃, free base) δ 1.15 (dd, 6H), 1.3 (d, 6H), 1.35–2.15 (m, 6H), 2.85 (m, 3H), 3.05 (m, 1H), 3.25 (d, 1H), 3.45 (d, 1H), 3.5 (s, 3H), 3.7 (d, 1H), 3.9 (d, 1H), 6.0 (s, 1H), 6.7 (d, 1H), 7.0 (d, 1H), 7.15–7.35 (m, 6H).

Mass Spectrum (m/e, %): 446 (M+, 40), 232 (100).

EXAMPLE 14

(2S,3S)-[5-(3,5-Dimethylthiophen-2-yl)-2-methoxybenzyl]-(2-phenylpiperidin-3-yl)aminedihydrochloride M.p. 252°–254° C.

¹H NMR (CDCl₃, free base) δ 1.37–2.01 (m, 6H), 2.20 (s, 3H), 2.38 (d, 3H), 2.8 (m, 2H), 3.27 (d, 2H), 3.50 (d, 1H), 3.85 (s, 3H) , 3.90 (d, 1H), 6.3 (d, 1H) , 6.72 (d, 1H) , 7.03 (m, 2H), 7.2–7.32 (m, 5H).

Mass Spectrum (m/e, %): 408 (M+2, 30), 407 (M+1, 100).

Anal. calc'd for $C_{25}H_{30}N_2OS \cdot 2HCl$: C, 62.62; H, 6.73; N, 5.84. Found: C, 62.29; H, 6.44; N, 5.91.

EXAMPLE 15

(2S,3S)-(6-Methoxy-2,3-dimethyl-benzorbithiophen-7-ylmethyl)-(2-phenylpiperidin-3-yl)amine dihydrochloride hydrate M.p. 240°–244° C.

¹H NMR (CDCl₃, free base) δ 1.35–2.10 (m, 5H), 2.25 (s, 3H), 2.3 (m, 1H), 2.4 (s, 3H), 2.8 (m, 2H), 3.3 (d, 1H), 3.5 (s, 3H), 3.75 (d, 1H), 3.9 (S+d, 2H), 6.8 (d, 1H), 7.2 (m, 5H), 7.35 (d, 1H).

Mass Spectrum (m/e, %): 381 (M+1, 100).

Anal. calc'd for $C_{23}H_{28}N_2OS \cdot HCl \cdot 1/4H_2O$: C, 65.54; H, 7.05; N, 6.65. Found: C, 65.47; H, 7.02; N, 6.56.

EXAMPLE 16

(1SR,2SR,3SR,4RS)-(2-Benzhydryl-1-aza-bicyclor2.2.1]hept-3-yl)-(6-methoxy-2-methyl-benzoxazol-5-ylmethyl)-amine A. (1SR,2SR,3SR,4RS)-(2-Benzhydryl-1-aza-bicyclo[2.2.1]hept-3-yl)-(6-methoxy-2-methyl-benzoxazol-5-ylmethylene)-amine.

(1SR,2SR,3SR,4RS)-(2-Benzhydryl-1-aza-bicyclo[2.2.1]hept-3-yl)-amine (54 mg, 0.194 mmol) was dissolved in toluene (35 mL) and was treated with 37 mg (0.194 mmol) of 6-methoxy-2-methylbenzoxazol-5-ylcarboxaldehyde. The reaction mixture was heated under reflux over a Dean-Stark trap for 26 hours. Analysis of the NMR spectrum from a small reaction aliquot indicated product formation was complete. The solution was evaporated in vacuo to provide the imine as a crude oil which was used directly in the next step without purification.

B. (1SR,2SR,3SR,4RS)-(2-Benzhydryl-1-aza-bicyclo[2.2.1]hept-3-yl)-(6-methoxy-2-methyl-benzoxazol-5-ylmethyl)-amine The crude imine from above was taken into 25 mL of dichloroethane and treated with 58 mg (0.272 mmol) of sodium triacetoxyborohydride. The mixture was stirred overnight (16 hours). Thin layer analysis ($CH_2Cl_2$:methanol (MeOH):concentrated ammonium hydroxide($NH_4OH$)— 94:5:1) indicated the reaction was complete. Reaction quenching with 20 mL of saturated aqueous sodium bicarbonate solution was followed by dilution with methylene chloride, extraction and drying. The organic phase was evaporated in vacuo to afford 130 mg of an oil. The crude product was chromatographed on silica gel eluting with a mixture of methylene chloride, methanol and aqueous ammonium hydroxide (98:1:1) to afford 90 mg of free base. The dihydrochloride salt was formed after dissolution of the free base in ether and treatment with saturated HCl gas, also in ether. The crude salt was obtained by direct evaporation of this reaction mixture. The residue was taken up in methanol (1 mL), clarified and treated with ether until the cloud point. The mixture was stirred overnight, whereupon crystallization occurred. The resulting solid (35 mg) was isolated by filtration.

$^1$H NMR (250 MHz, $CDCl_3$) δ 7.35 –7.06 (m, 12H), 6.81 (s, 1H), 4.18 (d, 1H, J=12.2 Hz), 3.76 (d, 1H, J=13.7 Hz), 3.52 (s, 3H), 3.51–3.40 (obsc. m, 1H), 3.43 (d, 1H, J=13.5 Hz), 3.08 (br.d, 1H, J=9.1 Hz)q, 2.76–2.60 (obsc. m, 2H), 2.60 (s, 3H), 250–2.40 (m, 1H), 2.17 (d, 1H, J=9.5 Hz), 1.75–1.55 (m, 2H), 1.12–1.0 (m, 1H).

$^{13}$C NMR (62.9 MHz, $CDCl_3$) δ 162.4, 155.5, 150.7, 145.8, 143.7, 134.1, 129.0, 128.9, 128.5, 127.7, 127.3, 126.4, 125.8, 124.9, 119.6, 92.7, 72.1, 63.3, 56.1, 55.7, 54.9, 50.8, 47.8, 41.4, 26.9, 14.5.

IR dihydrochloride salt (neat) λ 3000 (br), 2550 (br), 1620, 1580, 1500, 1480, 1460, 1440, 1380, 1350, 1310, 1210, 1150, 1120 $cm^{-1}$.

FAB MS: m/e 454 (m+1).

The title compounds of Examples 17 and 18 were prepared using procedures analogous to those of Examples 1 through 16.

EXAMPLE 17

(1SR,2SR,3SR,4RS)-(2-Benzhydryl-1-aza-bicyclo[2.2.1]hept-3-yl)-(6-methoxy-3-methyl-benzo[d]isoxazol-5-ylmethyl)amine $^1$H NMR (250 MHz, $CDCl_3$) δ 7.30–7.06 (m, 12H), 7.00 (s 1H), 6.81 (s, 1H), 4.28 (d, 1H, J=12.1 Hz), 3.75 (d, 1H, J=13.7 Hz), 3.61 (s, 3H), 3.53–3.46 (obsc. ma, 1H), 3.45 (d, 1H, J=13.7 Hz), 3.07 (br.d, 1H, J=9.6 Hz), 2.73 (dd, 2H, J=15.1 Hz, J=8.3 Hz), 2.65 (d, 1H, J=4.9 Hz), 2.53 (s, 3H), 2.53–2.41 (m, 1H), 2.18 (d, 1H, J=9.6 Hz), 1.7–1.5 (ma, 2H), 1.14–1.07 (m, 1H).

$^{13}$C NMR (75.5 MHz, $CDCl_3$) δ 163.8, 159.9, 154.5, 145.5, 143.7, 128.8, 128.4, 127.7, 127.2, 126.8, 125.2, 125.5, 120.4, 114.5, 90.9, 72.0, 63.8, 55.9, 55.7, 54.7, 50.7, 47.7, 41.4, 26.8, 10.0.

IR (neat) λ 3340, 2950, 1620, 1600, 1490, 1470, 1450, 1380, 1340, 1270, 1190, 1150 $cm^{-1}$.

HRMS calc'd for $C_{29}H_{32}N_3O_2$: 454.2487. Found: 454.2522.

EXAMPLE 18

(2S,3S)-(6-Methoxy-2-methyl-benzothiazol-5-ylmethyl)-(2-phenylpiperidin-3-yl)-amine $^1$H NMR (250 MHz, $D_2O$) dihydrochloride salt δ 7.63 (s, 1H), 7.57–7.55 (m, 1H), 7.49–7.40 (m, 1H), 7.36–7.25 (m, 3H), 7.12–7.09 (m, 2H), 4.89–487 (d, 1H, J=3.6 Hz), 4.47–4.42 (d, 1H, J=13.3 Hz), 4.17–412 (d, 1H, J=13.2 Hz), 4.05–4.02 (m, 1H), 3.71–3.61 (obsc. m, 1H), 3.61 (3H, s), 338–323 (m, 1H), 2.80 (3H, s), 2.54–247 (1H, m), 2.29–220 (2H, m), 2.11–1.99 (3H, m).

IR dihydrochloride salt (neat) λ 2700 br, 1610, 1560, 1520, 1460, 1430, 1420, 1280, 1220, 1050 $cm^{-1}$.

HRMS calc'd for $C_{21}H_{26}N_3OS$: 368.1791. Found: 368.17668.

EXAMPLE 19

(2S,3S-[5-(2,5-Dimethylpyrrol-1-yl)-2-methoxybenzyl]-(2-phenylpiperidin-3-yl)amine A. 2-Methoxy-5-nitrobenzaldehyde A mixture of 2.5 grams (13.5 mmol) of 2-chloro-5-nitrobenzaldehyde (Aldrich Chem. Co.) in 250 mL of $CH_3OH$ was treated with 2.92 grams (54.1 mmol) of sodium methoxide, refluxed for 16 hours and allowed to cool to room temperature. After removal of the solvent in vacuo, the residue was suspended in water, treated with 2N HCl (adjusting to pH <5) and extracted into methylene chloride. After drying over $MgSO_4$, the solvent was removed in vacuo to give a yellow solid, 2.02 grams (83%).

$^1$H-NMR ($CDCl_3$) δ 4.1 (s, 3H), 7.2 (d, 1H), 8.5 (dd, 1H)), 8.7 (d, 1H), 10.5 (s, 1H).

B. (2S,3S)-3-(2-Methoxy-5-nitrobenzyl)amino-2-phenylpiperidine

A mixture of 0.63 grams (3.48 mmol) of the above aldehyde and 0.60 grams (3.4 mmol) of (2S,3S)-3-amino-2-phenylpiperidine (prepared as described in U.S. patent application 724,268, filed on Jul. 1, 1991) in 60 mL of toluene was refluxed under nitrogen for 18 hours with a Dean-Stark apparatus to remove the water generated in the reaction. The toluene was then removed in vacuo and the oily residue was redissolved in 50 mL of methanol ($CH_3OH$), stirred under nitrogen for 1 hour and treated with 0.16 grams (4.23 mmol) of sodium borohydride. After stirring for 24 hours at 25° C., the solvent was evaporated in vacuo and the residue was treated with 50 mL of water, stirred for 1 hour and extracted with methylene chloride. The organic extracts were combined, dried over $MgSO_4$ and concentrated in vacuo to a pale orange oil. Chromatography on silica gel using concentrated ammonium hydroxide ($NH_4OH$): $CH_3OH$: $CH_2Cl_2$ (1:5:94) gave the title intermediate as a pale orange oil, 0.99 grams (85%).

$^1$H NMR ($CDCl_3$) δ 1.4 (d, 1H), 1.6 (tt, 1H), 1.7–1.95 (m, 3H), 2.05 (d, 1H), 2.75 (t, 2H), 3.15 (d, 1H), 3.35 (d, 1H), 3.55 (s, 1H), 3.65 (d, 1H), 3.85 (d, 1H), 6.65 (d, 1H), 7.2 (m, 5H), 7.9 (d, 1H), 8.0 (dd, 1H).

Mass Spectrum (m/e, %): 342 (m+1, 100%), 312 (10), 177 (16), 158 (14).

C. (2S,3S)-3-(5-Amino-2-methoxybenzyl)amino-2-phenylpiperidine

A solution of 0.3 grams (0.88 mmol) of the preceding compound in 10 mL of ethyl acetate (EtOAc) was treated with 0.11 grams of 10% palladium on carbon and hydrogenated in a Parr Shaker apparatus at an initial hydrogen pressure of 45 psi for a total of 4 hours. The reaction mixture was filtered through a pad of diatomaceous earth (d.e.) and the d.e. cake washed with additional EtOAc. The combined organics were concentrated in vacuo to give a pale orange oil, 0.33 grams.

$^1$H NMR ($CDCl_3$) δ 1.5 (m, 1H), 1.7 (m, 1H), 2.0 (m, 1H), 2.2 (m, 1H), 2.7–2.9 (m, 6H), 3.3 (m, 1H), 3.4 (d+s, 4H), 3.6 (d, 1H), 3.9 (d, 1H)), 6.3 (d, 1H), 6.4–6.6 (m, 2H), 7.2–7.4 (m, 5H).

D. (2S, 3S)-[5-(2,5-Dimethylpyrrol-1-yl)-2-methoxybenzyl]-2-(2-phenylpiperidin-3-yl)amine The above amine (0.33 grams) from part C in 12 mL of toluene was treated with 0.15 mL (1.28 mmol) of acetonylacetone and refluxed with a Dean-Stark apparatus for 2 hours. After cooling to 25° C., the solvent was removed in vacuo to give a yellow oil. Chromatography on silica gel using concentrated $NH_4OH:CH_3OH:CH_2Cl_2$ (1:5:94) gave a clear oil, 198 mg. The oil was converted to the hydrochloride salt of the title compound by suspending the free base in $CH_2Cl_2$ and treating it with 257 gL of 4M HCl in dioxane (2 equivalents), stirring at 25° C. for 20 min, filtering and drying the solid in vacuo to give a light yellow solid, 0.19 grams.

M.P. 217° C. (decomp).

$^1$H NMR (CDCl$_3$, free base) δ 1.4 (m, 1H), 1.8 (m, 1H), 1.8 (bs, 1H), 1.9 (m, 1H), 2.0 (s, 6H), 2.1 (m, 1H), 2.8 (m, 2H), 3.3 (m, 1H), 3.4 (d, 1H), 3.6 (s, 3), 3.8 (d, 1H), 3.9 (d, 1H), 5.9 (s, 2H), 6.7 (d, 1H), 6.9 (d, 1H), 7.0 (dd, 1H), 7.3 (m, 5H).

Mass spectrum: (m/e, %) 390 (m+1), 270.

Anal. calc'd for $C_{25}H_{31}N_3O.2HCl.1/3CH_2Cl_2$: C, 62.00; H, 6.91; N, 8.56. Found: C, 62.07; H, 6.86.; N, 8.21.

EXAMPLE 20

(2S,3S)-(6-Methoxy-2-phenyl-benzothiazol-5-ylmethyl)-(2-phenyl-piperidin-3-yl)-amine dihydrochloride salt A. Methyl-2-methoxy-5-nitrobenzoate A 500 ml round bottom flask was charged with 5.35 grams of 60% sodium hydride dispersion and the solid was washed twice with hexane and decanted (under nitrogen). The residue was suspended in 200 mL of dimethylformamide (DMF), cooled to 0° C. and was treated with 11 grams (60 mmol) of 2-hydroxy-5-nitrobenzoic acid. The reaction mixture was stirred for 1 hour at 0° C. The mixture was then treated with 17 mL (180 mmol) dimethyl sulfate and was allowed to warm to room temperature while stirring for 1.5 hours. An additional 17 mL of dimethyl sulfate was added and the reaction was stirred overnight at room temperature. The mixture was diluted with 1.5 L ethyl acetate and was washed with 400 ml of 0.75M aqueous sodium hydroxide (NaOH) solution followed by 400 mL of saturated bicarbonate solution, 400 mL of water and 500 mL of saturated brine. The organic phase was dried and evaporated. There was obtained 11.6 grams of the desired product as yellow flakes. The material was generally used without purification.

Mass Spectrum: (m/e) 212 (m+1)

B. Methyl-2-methoxy-5-aminobenzoate

A 2 liter Parr Bottle was charged with 11.6 grams (55 mmol) methyl-2-methoxy-5-nitrobenzoate, 450 mL of methanol and 150 mL of tetrahydrofuran (THF). Platinum oxide was added (460 mg) and the mixture was hydrogenated under 45 psi hydrogen for 1 hour. The reaction mixture was filtered through Celite® (diatomaceous earth) and evaporated. The reaction mixture was diluted with 500 mL of methylene chloride, and then washed with water and brine. The organic phase was dried and evaporated (9.9 grams). This material was used without further purification.

Mass Spectrum m/e 181 (m+)

C. Methyl-2-methoxy-5-benzamidobenzoate

A solution of 9.92 grams (55 mmol) of methyl-2-methoxy-5-aminobenzoate was taken up in 250 ml methylene chloride, treated with 8.4 mL (61 mmol) triethylamine and cooled to 0° C. The reaction mixture was then treated with 8.1 grams (57 mmol) benzoyl chloride in a dropwise fashion. The reaction mixture was stirred for 30 minutes while warming to room temperature. The reaction mixture was diluted with 500 mL of methylene chloride, washed with 200 mL saturated bicarbonate solution and then rewashed with water and brine. The organic phase was dried and evaporated to a flaky white solid (15.7 grams). This material was used without further purification.

Mass Spectrum: m/e 286 (m+1)

D. Methyl-2-methoxy-5-benzthioamido-benzoate

A 2 liter round bottom flask was charged with 15.7 grams (55 mmol) methyl-2-methoxy-5-benzamidobenzoate and 22.2 grams (55 mmol) of Lawesson's reagent followed by 500 mL of toluene. The reaction mixture was heated under reflux for 1.5 hours. The mixture was diluted with 500 mL of ethyl acetate, and washed with 250 mL of saturated aqueous bicarbonate solution, followed by washes with water and brine. The organic layer was dried over sodium sulfate, filtered and evaporated. The residue was chromatographed on silica eluting with 96/4 methylene chloride—ether. There was obtained 14.8 grams (89%) of desired material.

E. Methyl-6-methoxy-2-phenyl-5-benzothiazolcarboxylate

A 2 liter round bottom flask was charged with 81 grams (246 mmol) potassium ferricyanide in 300 mL of water, the solution was warmed to 55° C. A solution of 14.78 grams (49 mmol) methyl-2-methoxy-5-benzthioamido-benzoate in 200 mL of methanol and 100 mL aqueous sodium hydroxide solution [13.7 gm (343 mmol) NaOH/100 mL] was then added. A yellow precipitate was soon deposited. The mixture was stirred at 60° C. for 1.5 hours. The reaction mixture was partitioned between 1 liter ethyl acetate and 300 mL 3.4N HCl (aqueous). The organic phase was washed with water and brine solution and then dried over sodium sulfate. After filtration, the filtrate was evaporated and the residue, as a mixture of carboxylates, was used directly in the next step. (affords 12.9 grams crude)

F. 6-Methoxy-2-phenyl-5-hydroxymethylbenzothiazole

A 1 liter round bottom flask was charged with 12.88 grams (45.2 mmol) of methyl-6-methoxy-2-phenyl-5-benzothiazolecarboxylate (as part of a mixture of regioisomeric carboxylates) in 600 mL of dry tetrahydrofuran (THF). This solution was cooled to 0° C. and treated with 67.8 mL (67.8 mmol) of a 1.0M solution of lithium aluminum hydride in THF. The dark reaction mixture was stirred for 5 hours under nitrogen. The reaction was worked up by the careful dropwise addition of a saturated aqueous solution of sodium sulfate until a granular precipitate formed. The suspension was filtered and evaporated. The residue was dissolved in ethyl acetate and washed with water and saturated brine solution. The organic phase was dried over sodium sulfate and evaporated. This product was used directly in the next step. (10.94 grams crude yield)

G. 6-Methoxy-2-phenyl-benzothiazol-5-aldehyde

A solution of 10.94 grams (40.4 mmol) 6-methoxy-2-phenyl-5-hydroxymethylbenzothiazole (as part of a mixture of regioisomeric alcohols) in 600 mL of methylisobutyl ketone was treated with 42 grams (484 mmol) of manganese dioxide. The mixture was heated under reflux for 1.5 hours and was then filtered through Celite®. The filtrate was evaporated in vacuo and the residue was chromatographed on silica (elution with 9/1 hexane/ethyl acetate). Mixed fractions were rechromatographed on silica using 95/5 hexane/ethyl acetate to afford a total of 2.43 grams of the desired aldehyde.

Mass Spectrum: m/e 270 (m+1)

H. (2S,3S)-(6-Methoxy-2-phenyl-benzothiazol-5-ylmethyl)-(2-phenyl-piperidin-3-yl)-amine A round bottom flask equipped with a Dean Stark water separator and condenser was charged with 0.96 grams (3.6 mmol) 6-methoxy-2-phenyl-benzothiazol-5-aldehyde and 0.57 grams (3.2 mmol) of (2S, 3S)-2-phenyl-3-aminopiperidine in 90 mL of hours. The reaction mixture was evaporated in vacuo and the residue was redissolved in 90 mL of 1,2-dichlorethane. The solution was treated with 0.89 grams (4.2 mmol) of sodium triacetoxyborohydride and was stirred for 16 hours at room temperature. The reaction mixture was diluted with methylene chloride (600 mL) and washed with 150 mL of bicarbonate solution, 150 mL of water and finally with 150 mL of saturated brine solution. The organic phase was dried over sodium sulfate, filtered and evaporated. The residue was chromatographed on silica gel eluting with 97/2/1 methylene chloride, methanol, conc. aqueous ammonium hydroxide solution. Product containing fractions were combined, evaporated and crystallized from hot ether—MeOH to afford 1.1 grams (80%) of the desired product.

Mass Spectrum: m/e 430 (m+1)

I. (2S,3S)-(6-Methoxy-2-phenyl-benzothiazol-5-ylmethyl)-(2-phenyl-piperidin-3-yl)-aminedihydrochloride salt To a flame dried flask was added 20 mL of methanol and 1.97 mL (27.4 mmol) of acetyl chloride by slow dropwise addition. The solution was stirred for 10 min. at room temperature. A solution of (2S,3S)-(6-methoxy-2-phenyl-benzothiazol-5-ylmethyl)-(2-phenyl-piperidin-3-yl)-amine 2.35 grams (5.4 mmol) in methanol (prepared by warming) was then added to the reaction mixture prepared above. The resulting solution was stirred for 10 min. and then evaporated in vacuo. The residue was taken up in 500 mL of methanol, heated under reflux and filtered. The resulting solution was treated with 200 mL of diethyl ether and was allowed to stand at 5° C. to effect crystallization. There was obtained 2.55 grams of the hydrochloride salt (94%).

Analysis: Calc'd for $C_{26}H_{27}N_3OS.2$ HCl: C, 62.15; H; 5.82; N; 8.36. Found: C, 62.17; H, 5.89; N, 8.31.

The title compounds of Examples 21–25 were prepared using procedures analogous to that of Example 20.

EXAMPLE 21

(2S,3S)-(6-Methoxy-2-cyclopropyl-benzothiazol-5-ylmethyl)-(2-phenylpiperidin-3-yl)-amine Mass Spectrum: m/e 394 (m+1)

EXAMPLE 22

(2S,3S)-(6-Methoxy-2-tert-butyl-benzothiazol-5-ylmethyl)-(2-phenylpiperidin-3-yl)-amine HRMS calc'd for $C_{24}H_{31}N_3OS$: 409.2181. Found: 409.22240.

EXAMPLE 23

(2S,3S)-(6-Isopropoxyoxy-2-phenyl-benzothiazol-5-ylmethyl)-(2-phenylpiperidin-3-yl)-amine HRMS calc'd for $C_{28}H_{31}N_3OS$: 457.2181. Found: 457.21684.

EXAMPLE 24

(2S,3S)-(6-Isopropoxyoxy-2-methyl-benzothiazol-5-ylmethyl)-(2-phenylpiperidin-3-yl)-amine HRMS calc'd for $C_{23}H_{29}N_3OS$: 395.2025. Found: 395.20059.

EXAMPLE 25

(2S,3S)-(6-Trifluoromethoxy-2-methyl-benzothiazol-5-ylmethyl)-(2-phenylpiperidin-3-yl)-amine HRMS calc'd for $C_{21}H_{22}F_3N_3OS$: 421.1431. Found: 421.14432.

We claim:

1. A compound of the formula

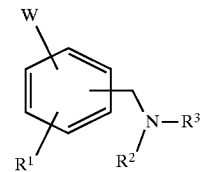

or a pharmaceutically acceptable salt thereof;

W is hydrogen, $(C_1-C_6)$alkyl optionally substituted with from one to three fluorine atoms, $-S(O)_v-(C_1-C_6)$ alkyl wherein v is zero, one or two, halo, benzyloxy or $(C_1-C_6)$alkoxy optionally substituted with from one to three fluorine atoms;

$R^1$ is a 4, 5 or 6 membered heterocyclic ring containing from one to three heteroatoms selected from oxygen, nitrogen and sulfur, wherein said heterocyclic ring contains from zero to three double bonds and is optionally substituted with one or two substituents independently selected from $(C_1-C_6)$ alkyl optionally substituted with from one to three fluorine atoms and $(C_1-C_6)$ alkoxy optionally substituted with from one to three fluorine atoms;

$R^2$ is hydrogen or $-CO_2(C_1-C_{10})$alkyl;

$R^3$ is

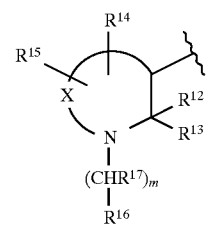

X is $(CH_2)_q$ wherein q is an integer from 1 to 6, and wherein any one of the carbon—carbon single bonds in said $(CH_2)_q$ is optionally replaced by a carbon—carbon double bond, and wherein any one of the carbon atoms of said $(CH_2)_q$ is optionally substituted with $R^{14}$, and wherein any one of the carbon atoms of said $(CH_2)_q$ is optionally substituted with $R^{15}$;

m is an integer from 0 to 8, and any one of the carbon—carbon single bonds of $(CH_2)_m$, wherein both carbon atoms of such bond are bonded to each other and to another carbon atom in the $(CH_2)_m$ chain, is optionally replaced by a carbon—carbon double bond or a carbon—carbon triple bond, and any one of the carbon atoms of said $(CH_2)_m$ is optionally substituted with $R^{17}$;

$R^{12}$ is a radical selected from hydrogen, $(C_1-C_6)$ straight or branched alkyl, $(C_3-C_7)$cycloalkyl wherein one of the carbon atoms is optionally replaced by nitrogen, oxygen or sulfur; aryl selected from biphenyl, phenyl, indanyl and naphthyl; heteroaryl selected from thienyl, furyl, pyridyl, thiazolyl, isothiazolyl, oxazolyl, isoxazolyl, triazolyl, tetrazolyl and quinolyl; phenyl- ($C_2$–$C_6$)alkyl, benzhydryl and benzyl, wherein the point of attachment on $R^{12}$ is a carbon atom unless $R^{12}$ is hydrogen, and wherein each of said aryl and heteroaryl groups and the phenyl moieties of said benzyl, phenyl-($C_2$–$C_6$)alkyl and benzhydryl is optionally substituted with one or more substituents independently selected from halo, nitro, ($C_1$–$C_{10}$)alkyl optionally substituted with from one to three fluorine atoms, ($C_1$–$C_{10}$) alkoxy optionally substituted with from one to three fluorine atoms, amino, hydroxy-($C_1$–$C_6$)alkyl, ($C_1$–$C_6$) alkoxy-($C_1$–$C_6$)alkyl, ($C_1$–$C_6$)alkylamino, —C(O)O ($C_1$–$C_6$ alkyl), —($C_1$–$C_6$ alkyl)C(O)($C_1$–$C_6$ alkyl), —OC(O)($C_1$–$C_6$ alkyl), —($C_1$–$C_6$ alkyl)C(O)O($C_1$–$C_6$ alkyl), —($C_1$–$C_6$ alkoxy)C(O)($C_1$–$C_6$ alkyl), —C(O) ($C_1$–$C_6$ alkyl), —N($C_1$–$C_6$ alkyl)($C_1$–$C_6$ alkyl), —C(O)NH($C_1$–$C_6$ alkyl), —NHC(O)H, and —NHC (O)($C_1$–$C_6$ alkyl); and wherein one of the phenyl moieties of said benzhydryl may optionally be replaced by naphthyl, thienyl, furyl or pyridyl;

$R^{13}$ is hydrogen, phenyl or ($C_1$–$C_6$)alkyl;

or $R^{12}$ and $R^{13}$, together with the carbon to which they are attached, form a saturated carbocyclic ring having from 3 to 7 carbon atoms wherein one of said carbon atoms that is neither the point of attachment of the spiro ring nor adjacent to it may optionally be replaced by oxygen, nitrogen or sulfur;

$R^{14}$ and $R^{15}$ are each independently selected from hydrogen, hydroxy, halo, amino, oxo (=O), cyano, hydroxy-($C_1$–$C_6$)alkyl, ($C_1$–$C_6$)alkoxy-($C_1$–$C_6$)alkyl, ($C_1$–$C_6$)alkylamino, —C(O)O($C_1$–$C_6$ alkyl), —OC(O) ($C_1$–$C_6$ alkyl), —($C_1$–$C_6$ alkyl)C(O)($C_1$–$C_6$ alkyl), —($C_1$–$C_6$ alkyl)C(O)O($C_1$–$C_6$ alkyl), —($C_1$–$C_6$ alkoxy)C(O)($C_1$–$C_6$ alkyl), —C(O)($C_1$–$C_6$ alkyl), —N($C_1$–$C_6$ alkyl)($C_1$–$C_6$ alkyl), —C(O)NH($C_1$–$C_6$ alkyl), —NHC(O)H, —NHC(O)($C_1$–$C_6$ alkyl), and the radicals set forth in the definition of $R^{12}$;

$R^{16}$ is NHC(O)$R^{18}$, NHCH$_2$$R^{18}$, SO$_2$$R^{18}$, CO$_2$H or one of the radicals set forth in any of the definitions of $R^{12}$, $R^{14}$ and $R^{15}$;

$R^{17}$ is oximino (=NOH) or one of the radicals set forth in any of the definitions of $R^{12}$, $R^{14}$ and $R^{15}$; and $R^{18}$ is ($C_1$–$C_6$)alkyl, hydrogen, phenyl or phenyl-($C_1$–$C_6$) alkyl;

with the proviso that (a) when m is 0, one of $R^{16}$ and $R^{17}$ is absent and the other is hydrogen, (b) when $R^{14}$ and $R^{15}$ are attached to the same carbon atom, then either each of $R^{14}$ and $R^{15}$ is independently selected from hydrogen, fluoro, ($C_1$–$C_6$)alkyl, hydroxy-($C_1$–$C_6$)alkyl and ($C_1$–$C_6$)alkoxy-($C_1$–$C_6$)alkyl, or $R^{14}$ and $R^{15}$, together with the carbon to which they are attached, form a ($C_3$–$C_6$) saturated carbocyclic ring that forms a spiro compound with the nitrogen-containing ring to which they are attached; (c) $R^{12}$ and $R^{13}$ cannot both be hydrogen; and (d) when $R^{14}$ or $R^{15}$ is attached to a carbon atom of X that is adjacent to the ring nitrogen, then $R^{14}$ or $R^{15}$, respectively, must be a substituent wherein the point of attachment is a carbon atom.

2. A compound according to claim 1, wherein the substituents at positions "2" and "3" of the nitrogen containing ring of $R^3$ are in a cis configuration.

3. A compound according to claim 1, wherein $R^2$ is hydrogen, W is ($C_1$–$C_3$)alkoxy optionally substituted with from one to five fluorine atoms, and $R^1$ is thiazolyl, imidazolyl, thiadiazolyl, pyrrolyl, pyridyl, pyrimidinyl, pyrazolyl, thiophenyl or oxazolyl, and $R^1$ may optionally be substituted with one or two ($C_1$–$C_3$)alkyl moieties.

4. A compound according to claim 1, wherein $R^{12}$ is phenyl, each of $R^{13}$, $R^{14}$, $R^{15}$ and $R^{16}$ is hydrogen, m is zero and X is —(CH$_2$)$_3$—.

5. A compound according to claim 1 wherein each of $R^{13}$, $R^{14}$, $R^{15}$ and $R^{16}$ is hydrogen, m is zero, W is methoxy or isopropoxy, X is —(CH$_2$)$_3$— and $R^1$ is thiazolyl, imidazolyl, pyrrolyl, oxazolyl, pyridyl, pyrimidinyl, pyrazolyl, thiophenyl or thiadiazolyl.

6. A compound according to claim 1 that is selected from the group consisting of:

(2S,3S)-[5-(2,5-dimethyl-pyrrol-1 -yl)-2-methoxybenzyl] -(2-phenylpiperidin-3-yl)amine;

(2S,3S)-3-[2-methoxy-5-(2-thiazolyl)benzyl]amino-2-phenylpiperidine;

(2S,3S)-3-[5-imidazolyl-2-methoxybenzyl]amino-2-phenylpiperidine;

(2S,3S)-3-[2-methoxy-5-(2-oxopyrrolidinyl)benzyl] amino-2-phenylpiperidine;

(2S,3S)-3-[2-methoxy-5-(4-methyl-2-thiazolyl)benzyl]-amino-2-phenylpiperidine;

(2S,3S)-3-[2-methoxy-5-(1,2,3-thiadiazol-4-yl)benzyl]-amino-2-phenylpiperidine;

(2S,3S)-3-[2-methoxy-5-(5-oxazolyl)benzyl]amino-2-phenylpiperidine;

(2S,3S)-(2-methoxy-5-pyridin-2-ylbenzyl)-(2-phenylpiperidin-3-yl)amine;

(2S,3S)-(2-methoxy-5-pyrimidin-2-ylbenzyl)-(2-phenylpiperidin-3-yl)amine;

(2S,3S)-(2-methoxy-5-pyridin-3-ylbenzyl)-(2-phenylpiperidin-3-yl)amine;

(2S,3S)-[2-methoxy-5-(6-methylpyridin-2-yl)benzyl]-(2-phenylpiperidin-3-yl)amine;

(2S,3S)-[5-(3,5-dimethylpyrazol-I -yl)-2-methoxybenzyl] -(2-phenylpiperidin-3-yl)amine;

(2S,3S)-[2-methoxy-5-(3,4,5-trimethylpyrazol-1-yl) benzyl]-(2-phenylpiperidin-3-yl)amine;

(2S,3S)-[2-isopropoxy-5-(3,4,5-trimethylpyrazol-1-yl) benzyl]-(2-phenylpiperidin-3-yl)amine;

(2S,3S)-[5-(3,5-diisopropylpyrazol-1 -yl)-2-methoxybenzyl]-(2-phenylpiperidin-3-yl)amine;

(2S,3S)-[5-(3,5-dimethylthiophen-2-yl)-2-methoxybenzyl]-(2-phenylpiperidin-3-yl)amine; and the pharmaceutically acceptable salts of the foregoing compounds.

7. A pharmaceutical composition for treating or preventing a condition selected from the group consisting of inflammatory diseases, anxiety, urinary incontinence, gastrointestinal disorders, depression or dysthymic disorders, psychosis, pain, allergies, chronic obstructive airways disease, hypersensitivity disorders, vasospastic diseases, fibrosing and collagen diseases, reflex sympathetic dystrophy, addiction disorders, stress related somatic disorders, peripheral neuropathy, neuralgia, neuropathological disorders, disorders related to immune enhancement or suppression and rheumatic diseases in a mammal, comprising an amount of a compound according to claim 1 effective in preventing or treating such condition and a pharmaceutically acceptable carrier.

8. A method of treating or preventing a condition selected from the group consisting of inflammatory diseases anxiety, urinary incontinence, gastrointestinal disorders, depression or dysthymic disorders, psychosis, pain, allergies, chronic obstructive airways disease, hypersensitivity disorders, vasospastic diseases, fibrosing and collagen diseases, reflex sympathetic dystrophy, addiction disorders, stress related somatic disorders, peripheral neuropathy, neuralgia, neuropathological disorders, disorders related to immune enhancement or suppression and rheumatic diseases in a mammal, comprising administering to a mammal in need of such treatment or prevention an amount of a compound according to claim 1 effective in preventing or treating such condition.

9. A pharmaceutical composition for antagonizing the effects of substance P in a mammal, comprising a substance P antagonizing effective amount of a compound according to claim 1 and a pharmaceutically acceptable carrier.

10. A method of antagonizing the effects of substance P in a mammal, comprising administering to said mammal a substance P antagonizing effective amount of a compound according to claim 1.

11. A pharmaceutical composition for treating or preventing a condition in a mammal, the treatment or prevention of which is effected or facilitated by a decrease in substance P mediated neurotransmission, comprising an amount of a compound according to claim 1 effective in antagonizing the effect of substance P at its receptor site and a pharmaceutically acceptable carrier.

12. A method of treating or preventing a condition in a mammal, the treatment or prevention of which is effected or facilitated by a decrease in substance P mediated neurotransmission, comprising administering to a mammal in need of such treatment or prevention an amount of a compound according to claim 1, or a pharmaceutically acceptable salt thereof, effective in antagonizing the effect of substance P at its receptor site.

13. A pharmaceutical composition for treating or preventing a condition in a mammal, the treatment or prevention of which is effected or facilitated by a decrease in substance P mediated neurotransmission, comprising an amount of a compound according to claim 1, or a pharmaceutically acceptable salt thereof, effective in treating or preventing such condition and a pharmaceutically acceptable carrier.

14. A method of treating or preventing a condition in mammal, the treatment or prevention of which is effected or facilitated by a decrease in substance P mediated neurotransmission, comprising administering to a mammal in need of such treatment or prevention an amount of a compound according to claim 1 effective in treating or preventing such condition.

\* \* \* \* \*